(12) United States Patent
Fellenberg et al.

(10) Patent No.: US 7,650,343 B2
(45) Date of Patent: Jan. 19, 2010

(54) DATA WAREHOUSING, ANNOTATION AND STATISTICAL ANALYSIS SYSTEM

(75) Inventors: Kurt Fellenberg, Heidelberg (DE); Nicole Hauser, Heidelberg (DE)

(73) Assignee: Deutsches Krebsforschungszentrum Stiftung des Offentlichen Rechts, Heidelberg (DE)

( * ) Notice: Subject to any disclaimer, the term of this patent is extended or adjusted under 35 U.S.C. 154(b) by 115 days.

(21) Appl. No.: 10/263,114

(22) Filed: Oct. 2, 2002

(65) Prior Publication Data

US 2003/0200034 A1    Oct. 23, 2003

(30) Foreign Application Priority Data

Oct. 4, 2001    (EP) ................... 01123732

(51) Int. Cl.
  G06F 7/00    (2006.01)
  G06F 17/00    (2006.01)

(52) U.S. Cl. .................................... 707/100

(58) Field of Classification Search .............. 707/102, 707/104.1, 100; 702/20; 715/512
  See application file for complete search history.

(56) References Cited

U.S. PATENT DOCUMENTS

| | | | |
|---|---|---|---|
| 5,305,208 A * | 4/1994 | Doi et al. ..................... | 715/502 |
| 5,566,330 A * | 10/1996 | Sheffield ...................... | 707/4 |
| 5,832,496 A * | 11/1998 | Anand et al. ................. | 707/102 |
| 6,519,603 B1* | 2/2003 | Bays et al. ................... | 707/102 |
| 6,553,317 B1* | 4/2003 | Lincoln et al. ............... | 702/20 |
| 6,658,429 B2* | 12/2003 | Dorsett, Jr. ................... | 707/1 |
| 2002/0147725 A1* | 10/2002 | Janssen et al. ............... | 707/100 |
| 2003/0009295 A1* | 1/2003 | Markowitz et al. ........... | 702/20 |

FOREIGN PATENT DOCUMENTS

| | | |
|---|---|---|
| EP | 435478 A2 | 7/1991 |
| EP | 840240 A2 | 5/1998 |

OTHER PUBLICATIONS

Leon et al, 'Multivariate visualization in observation-based testing', Jun. 2000, ACM Press, Proceedings of the 22nd international conference on Software engineering, pp. 116-125.*

Schroeder, 'Integrated program measurement and documentation tools', Mar. 1984, IEEE Press, Proceedings of the 7th international conference on Software engineering, pp. 304-313.*

(Continued)

*Primary Examiner*—James Trujillo
*Assistant Examiner*—Marc Somers
(74) *Attorney, Agent, or Firm*—Kelly K. Reynolds; Steven J. Hultquist; Intellectual Property / Technology Law

(57) ABSTRACT

The present invention relates to a database storage structure for the storage of a plurality of results from an experiment on a sample. The database storage structure includes a result storage table for storing the results from the experiment, one or more first annotation storage tables for storing a first set of variables, and one or more second annotation storage tables for storing a second limited set of variables. The one or more second annotation storage tables are further coupled to one or more concordance tables for storing a concordance between the second limited set of variables and a second list of annotations.

25 Claims, 17 Drawing Sheets

OTHER PUBLICATIONS

David Eichmann et al., *Integrating Structured Database into the Web: The MORE System*, Computer Networks and ISDN Systems, vol. 27, pp. 281-288 (1994).

Douglas Bassett Jr. et al., *Gene Expression Informatics—It's All in Your Mine*, Nature Genetics Supplement, vol. 21, pp. 51-55 (Jan. 1999).

T. Beiβbarth et al., *Processing and Quality Control of DNA Array Hybridization Data*, Bioinformatics, vol. 16, No. 11, pp. 1014-1022 (2000).

Dari Shalon et al., *A DNA Microarray System for Analyzing Complex DNA Samples Using Two-color Fluorescent Probe Hybridization*, Genome Research, vol. 6, pp. 639-645 (1996).

Christian Schönbach et al., *Data Warehousing in Molecular Biology*, Briefings in Bioinformatics, vol. 1, No. 2, pp. 190-198 (May 2000).

Mark Schena, *Genome Analysis with Gene Expression Microarrays*, BioEssays, vol. 18, No. 5, pp. 427-431 (1996).

Mark Schena et al., *Quantitative Monitoring of Gene Expression Patterns with a Complementary DNA Microarray*, Science, vol. 270, pp. 467-470 (Oct. 20, 1995).

David Lockhart et al., *Expression Monitoring by Hybridization to High-Density Oligonucleotide Arrays*, Nature Biotechnology, vol. 14, pp. 1675-1680 (Dec. 1996).

David J. Lockhart and Elizabeth A. Winzeler, *Genomics, Gene Expression and DNA Arrays*, Nature, vol. 405, pp. 827-836 (Jun. 15, 2000).

Gregory G. Lennon and Hans Lehrach, *Hybridization Analyses of Arrayed cDNA Libraries*, TIG, vol. 7, No. 10, pp. 314-317 (Oct. 1991).

Javed Khan et al., *DNA Microarray Technology: The Anticipated Impact on the Study of Human Disease*, Biochemica et Biophsica Acta, vol. 1423, M17-M28 (1999).

Kurt Fellenger et al., *Correspondence Analysis Applied to Microarray Data*, PNAS, vol. 98, No. 19, pp. 10781-10786 (Sep. 11, 2001).

Olga Ermolaeva et al., *Data Management and Analysis for Gene Expression Arrays*, Nature Genetics, vol. 20, pp. 19-23 (Sep. 1998).

Michael Eisen et al., *Cluster Analysis and Display of Genome-Wide Expression Patterns*, Proc. Natl. Acad. Sci. USA, vol. 95, pp. 14863-14868 (Dec. 1998).

Joseph DeRisi et al., *Use of a cDNA Microarray to Analyze Gene Expression Patterns in Human Cancer*, Nature Genetics, vol. 14, pp. 457-460 (Dec. 1996).

Patrick Brown and David Botstein, *Exploring the New World of the Genome with DNA Microarrays*, Nature Genetics Supplement, vol. 21, pp. 33-37 (Jan. 1999).

Alvis Brazma et al., *One-Stop Shop for Microarray Data*, Nature, vol. 403, pp. 699-700 (Feb. 17, 2000).

C. Stoeckert et al., *A Relational Schema for Both Array-Based and SAGE Gene Expression Experiments*, Bioinformatics, vol. 17, No. 4, pp. 300-308 (2001).

John Aach et al., *Systematic Management and Analysis of Yeast Gene Expression Data*, Genome Research, vol. 10, pp. 431-445 (2000).

Chuck Ballard et al., Data Modeling Techniques for Data Warehousing (International Technical Support Organization of IBM, Feb. 1998).

* cited by examiner common_annotations array

1 – array_source [ 10 – self_made ]

2 – array_series [ ]

3 – array_individual [ ]

4 – array_support [ 14 – nylon ]

41 – spotted_material [ 17 – PCR ]

47 – readfile [ ]

7 – array_hybridisation [ ]

hybridisation

RNA_preparation

8 – material_source [ 21 – fresh ]

9 – preparation_of_total_RNA [ 24 – trizol ]

10 – preparation_of_PolyA+ [ 27 – none ]

Figure 2

More than or exactly 2x overunderrepresented:

```
annotation 2 array_series
    value 59 is 7x overrepresented (2/2 in cluster :   2/14 in total)
    value 61 is absent (0/2 in cluster : 12/14 in total)

annotation 3: array_individual
    value 1 is absent (0/2 in cluster :  2/14 in total)
    value 2 is absent (0/2 in cluster :  2/14 in total)
    value 3 is absent (0/2 in cluster :  2/14 in total)
    value 4 is absent (0/2 in cluster :  2/14 in total)
    value 5 is absent (0/2 in cluster :  4/14 in total)
    value 6 is 7x overrepresented (2/2 in cluster :  2/14 in total)

annotation 7: array_hybridisation
    value 5 is absent (0/2 in cluster :  1/14 in total)
    value 6 is absent (0/2 in cluster :  1/14 in total)

annotation 16: label incorporation rate
    value 44 is absent (0/2 in cluster :  1/14 in total)
    value 46 is absent (0/2 in cluster :  1/14 in total)
    value 51 is absent (0/2 in cluster :  2/14 in total)
    value 52 is 7x overrepresented (1/2 in cluster :  1/14 in total)
    value 56 is 7x overrepresented (1/2 in cluster :  1/14 in total)
    value 59 is absent (0/2 in cluster :  1/14 in total)
    value 68 is absent (0/2 in cluster :  1/14 in total)
    value 84 is absent (0/2 in cluster :  1/14 in total)
    value 87 is absent (0/2 in cluster :  2/14 in total)
    value 88 is absent (0/2 in cluster :  2/14 in total)
    value 93 is absent (0/2 in cluster :  1/14 in total)

annotation 17: total_activity
    value 26000000 is absent (0/2 in cluster :  1/14 in total)
    value 34000000 is absent (0/2 in cluster :  1/14 in total)
    value 35000000 is absent (0/2 in cluster :  1/14 in total)
    value 36000000 is absent (0/2 in cluster :  1/14 in total)
    value 38000000 is 7x overrepresented (1/2 in cluster :  1/14 in total)
    value 39000000 is absent (0/2 in cluster :  1/14 in total)
    value 43000000 is 7x overrepresented (1/2 in cluster :  1/14 in total)
    value 46000000 is absent (0/2 in cluster :  1/14 in total)
    value 56000000 is absent (0/2 in cluster :  1/14 in total)
    value 61000000 is absent (0/2 in cluster :  2/14 in total)
    value 65000000 is absent (0/2 in cluster :  1/14 in total)
    value 71000000 is absent (0/2 in cluster :  1/14 in total)
    value 80000000 is absent (0/2 in cluster :  1/14 in total)

annotation 39: experimentator
    value 104: bastuk is absent (0/2 in cluster :  2/14 in total)

annotation 1053: temporary_additive
    value 1123: none is absent (0/2 in cluster :  2/14 in total)

annotation 1055: incubation_period
    value 5 is absent (0/2 in cluster :  4/14 in total)
    value 10 is absent (0/2 in cluster :  2/14 in total)
    value 15 is absent (0/2 in cluster :  2/14 in total)
    value 20 is absent (0/2 in cluster :  2/14 in total)
    value 30 is 3.5x overrepresented (2/2 in cluster :  4/14 in total)
```

Figure 5

DATA WAREHOUSING, ANNOTATION AND STATISTICAL ANALYSIS SYSTEM

CROSS-REFERENCE TO RELATED APPLICATIONS

This application is filed under the provisions of 35 U.S.C. §119 and claims the priority of European Patent Application No. 01 123 732.8 filed Oct. 4, 2001.

FIELD OF THE INVENTION

The invention relates to a data warehouse which facilitates the inclusion of experiment annotations in statistical analysis.

DESCRIPTION OF RELATED ART

Microarray technology provides access to expression levels of thousands of genes at once, producing large amounts of data. These datasets are valuable only if they are annotated by sufficiently detailed experiment descriptions. However, in many databases a substantial number of these annotations is in free-text format and not readily accessible to computer aided analysis.

Analysis of microarrays provides insight into the transcriptional state of the cell (transcriptome) and measures the RNA levels for thousands of genes simultaneously as has been described in the papers by DeRisi et at., 1996; Khan et al., 1999; Brown and Botstein 1999; Lockhart and Winzeler, 2000. This is done by hybridising a labelled RNA sample to an array of either 'spotted' cDNA fragments or of oligonucleotides synthesized 'on chip' (see, for example, Lennon and Lehrach, 1991; Schena et al., 1995; Schena, 1996; Shalon et at., 1996; Lockhart et al., 1996). Ongoing sequencing projects promise to yield complete gene sets of most model organisms in the near future that can then be mounted on DNA chips. However the data produced need to be stored in a proper way to allow for global comparison as is discussed in Basset Jr. et al., 1999. This applies not only to the signal intensities for each item in an array but also to all available descriptions of the sample from which the RNA has been derived as well as all details of its treatment.

Several database projects are currently addressing these questions. While ExpressDB (Harvard, Aach et al. 2000) aims at storing data from nearly all available platforms, i.e. cDNA and oligonucleotide chips as well as SAGE, a different focus has been to develop systems for consistent description of the samples used and the genes mounted on the array. Examples of such databases include GeneX (from the NCGR), GEO (from the NCBI), ArrayDB (from NEGRI and described in Ermolaeva et at. 1998), ArrayExpress (from the Eel and described in Brazma et at, 2000)) and RAD (from the University of Pennsylvania and described in Stoeckert et at. 2001). The last named database project combines both objectives. So-called data warehouses are known in the art in which data are held in one or several databases. A warehouse then collects data from their storage databases and makes them fit into a unified data model (see, for example, Ballard et at. 1998; Schönbach et al., 2000). Typically, a warehouse will collect only a few 'important' attributes from each dataset. Such operations like transformations and extractions are recorded as meta data. The data warehouse may be de-normalized, i.e. it allows for redundancy in order to avoid frequent joining from distinct tables.

Also known in the art are various database structures for entering and accessing data. For example, European Patent Application EP-A-0 840 240 (NCR) teaches a system for performing analysis and segmentation of a computer database. European Patent Application EP-A-0 435 478 (Emtek Health Care System) discloses a further database which includes forms for entering data about patients. Finally an article by Eichmann et al "Integrating structured databases into the web: the MORE system" in Computer Networks and ISDN Systems, vol 27 (1994), pp281-288 teaches the design of a meta-data based repository. None of these publications is, however, directed towards the storage of results from an experiment on a sample.

Using currently available systems, most of the valuable information contained in experiment annotation is not taken into account for analysis. This is due to the fact that the annotations are stored in a way that is not readily accessible for multivariate statistical methods. For example, misspellings, different textual labelling of semantically identical items, ambiguous words whose meaning depends on the context all hinder the reliable use of annotations for statistical analysis.

SUMMARY OF THE INVENTION

There is therefore a need to provide a database structure, system and method which allows the direct comparison of experimental annotation between different datasets.

There is furthermore a need to ensure consistency of annotations between datasets annotated by different annotators.

There is yet a further need to avoid the need to parse free text annotations when analysing data.

These and other objects of the invention are solved by providing a database storage structure for the storage of a plurality of results from an experiment on a sample. The database storage structure includes a result storage table for storing the results from the experiment. It has furthermore one or more first annotation storage tables for storing a first set of variables. One or more second annotation storage tables for storing a second limited set of variables. The one or more second annotation storage tables are coupled to one or more concordance tables for storing a concordance between the second limited set of variables and a second list of annotations.

The use of a database storage structure with annotation tables having a limited set of variables taking a defined set of values allows easy analysis by statistical methods of the data. The formats include, but are not limited to, formats in which the results of the experiment that have a continuous range of values are discretized into discrete values. The key words could be, for example, derived from the ontology of the experiment or are a set of standard conditions for the experiment.

In order to keep the annotation concept flexible enough to include easily new attributes as well as new values, without the need to alter the analysing algorithms, the definitions for the annotations and their allowed values are stored as separate concordance tables in the database linked to the annotation tables. Using this structure, a fixed, 'hard-wired' structure is avoided that would be difficult to extend.

The list of annotations can comprise a list of annotations relating to the sample tested in the experiment, a list of annotations related to genes present in the experiment, a list of annotations relating to the conditions of the experiment, measurement values and/or identifiers to access data in public data bases.

The limited set of variables are in an enumerable or countable format which allows ready analysis, in particular statistical analysis, of the values. In one embodiment of the invention, the database storage structure is used to analyse the results of a microarray experiment and the result storage table stores the signal intensities of the spots of the microarray. The database storage structure can, however, be used to record data from other experiments.

The objects of the invention are also solved by providing a system comprising an experimental apparatus for performing an experiment, a storage device for storing the database storage structure, a processing unit connected to the microarray for reading the results from the experiment and passing them to the storage device, a further processing unit for statistically analysing the results in the database storage structure to produce statistically analysed results, and a display device for displaying the statistically analysed results.

The further processing units uses statistical analysis methods for analysing the results in the database storage. In one embodiment of the invention the methods used are correspondence analysis methods.

The system is further advantageously provided with an annotation device to allow an annotator to annotate the experimental results. In one embodiment, the annotation device includes a visual display unit and an annotation input device.

Additionally the system further comprises a selection device for selecting a subset of the results from the storage device. This can be done, for example, by selecting a selection of results displaying on the display device.

Advantageously, one or more subtables are used to temporarily store the results. At time intervals, e.g. overnight or during quiet periods, the results are transferred from the subtables to the result storage table. This improves the performance of the system.

Finally the objects of the invention are solved by providing a method for entering annotations into a database storage structure comprising a first step of accessing a concordance table to obtain a list of annotations, a second step of using the annotations to generate an input form, a third step of displaying the input form to an annotator, a fourth step of receiving data input by the annotator a fifth step of using the data and the concordance table to generate a set of variables, a sixth step of storing the set of variables in a storage.

This method substantially reduces the workload of the annotator by automating much of the annotation. The input form could, for example, include default values. The annotator is required to only change or enter the data once.

In one embodiment of the invention, the method further includes a step of analysing at least one of the set of variables using correspondence analysis techniques to produce an output set. The output set can be visualised, for example, on a visual display device.

The method of the invention further comprises a step of selecting at least a subset of the set of variables to allow only analysis of this subset. The method also provides a step of clustering the set of variables. This allows the user analysing the results to identify related groups of results.

The invention has been implemented as a set of organism-specific databases, namely for *Saccharomyces cerevisiae*, *Arabidopsis thaliana*, *Trypanosoma brucei*, *Neurospora crassa* and human tumor samples, While differing in the annotations used to describe the samples, these databases share a common structure and thus are accessed by the very same analysis algorithms. The invention is able to integrate all kinds of intensity data obtained from cDNA microarrays. It has been tailored for the need of the collaborating groups that use cDNA microarrays with either single-channel radioactive or multi-channel fluorescence readout.

Although the invention is described with respect to microarrays, it is equally applicable to any experimental or other data-collection system in which large numbers of data points need to be collected in a data warehouse, annotated and statistically analysed.

The invention integrates different data sources and data formats into a de-normalized structure, records meta data and enables unified access for analysis algorithms. However, there are no underlying so called 'operational' databases, and data are directly entered into the database storage. As a result, analysis of the entered data may be carried out immediately, enabling instant decisions about follow-up experiments to be made. There is furthermore no loss of information in experiment description. Annotations are not extracted by compliance to minimal standards, but entered directly at a level of detail chosen by the experimenter defining the annotations. All annotations are in an analysable form that avoids text mining that, as outlined above, frequently results in information loss.

BRIEF DESCRIPTION OF THE DRAWINGS

FIG. 2 shows an annotation input form.
FIG. 5 shows the frequency of characteristic annotation values for the hybridisations of FIG. 4.

DETAILED DESCRIPTION OF THE INVENTION

Figure 1A:
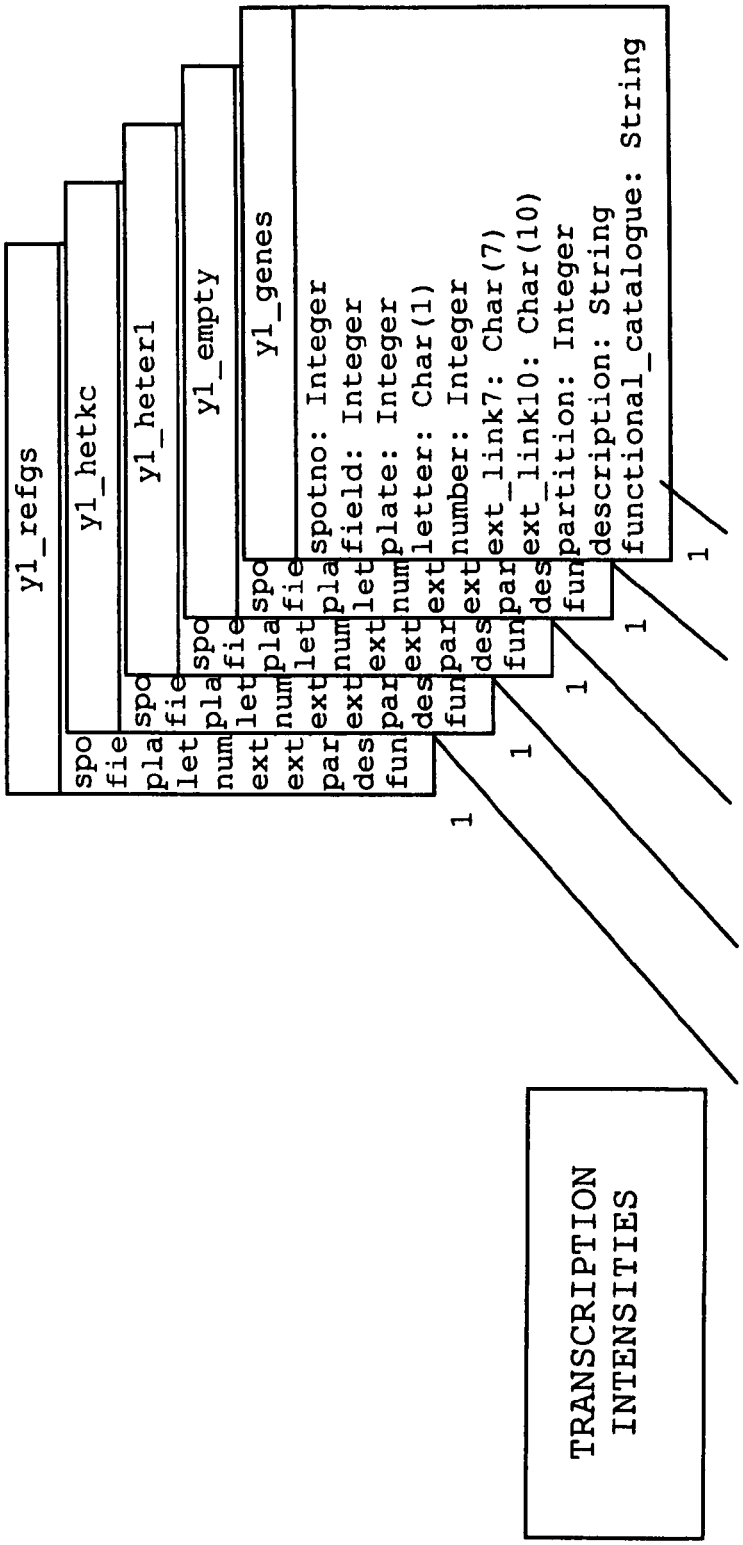
FIGS. 1*a* to 1*i* show an overview of the database structure.
Figure 1B:
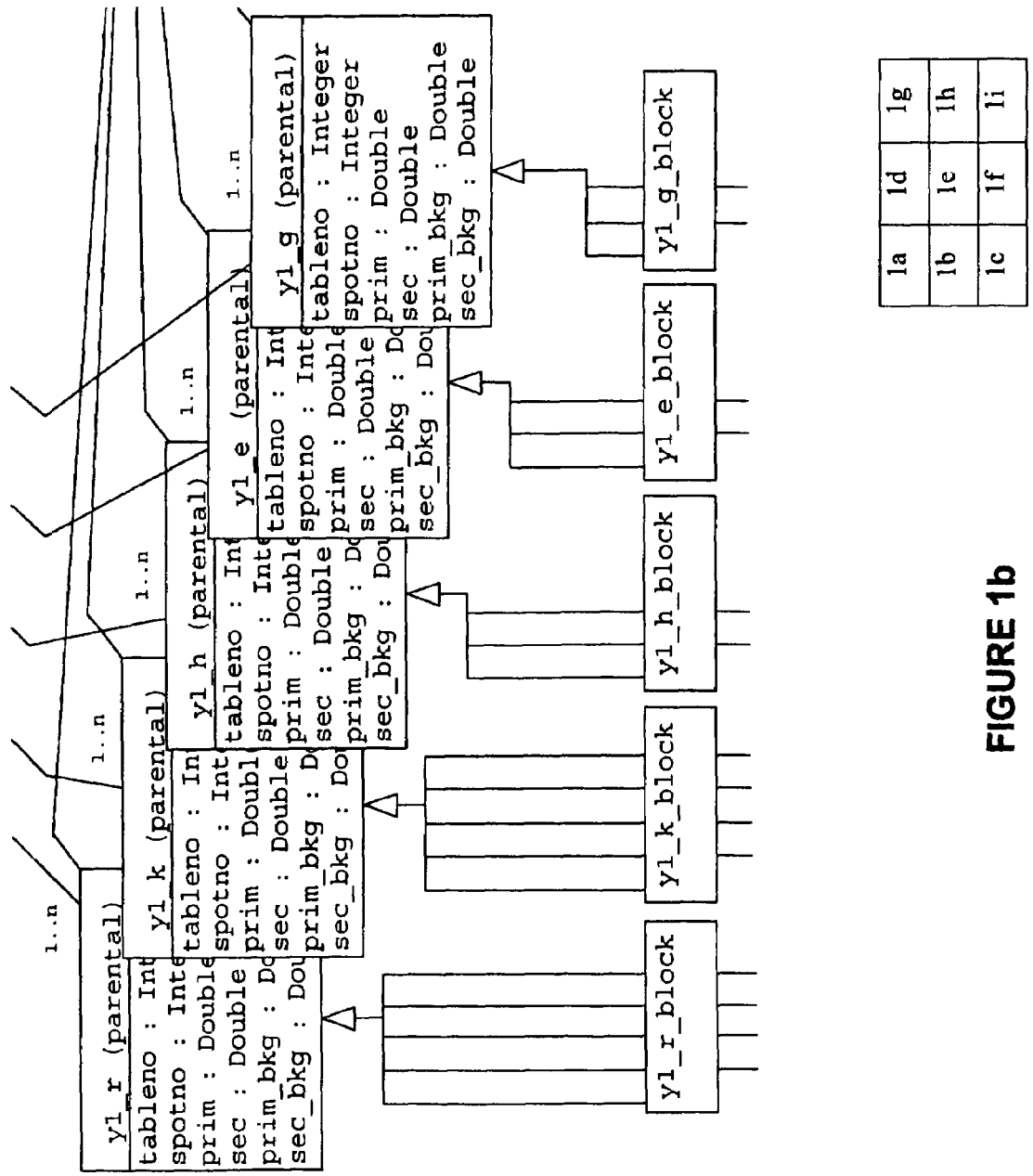
Figure 1C:
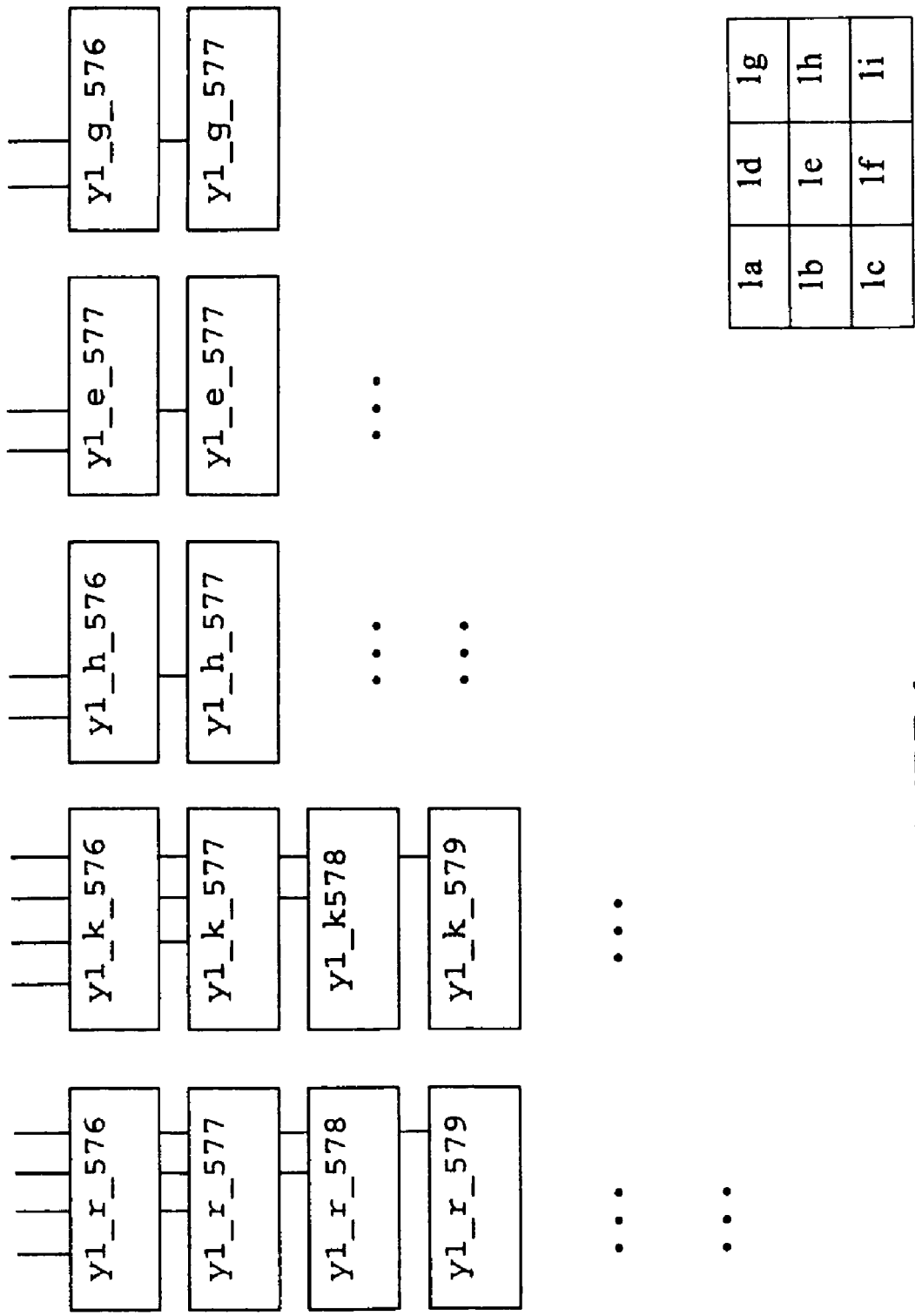
Figure 1D:
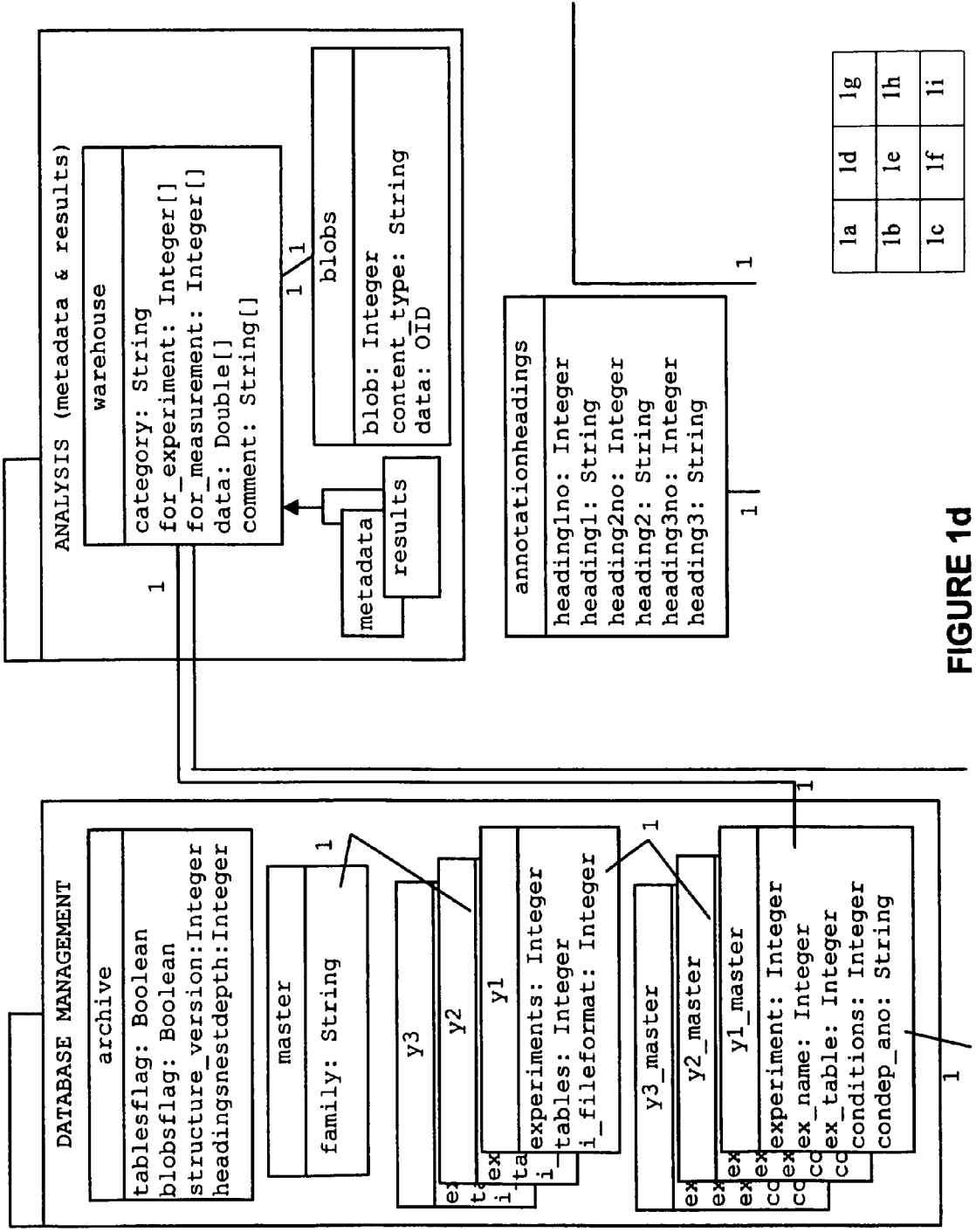
Figure 1E:
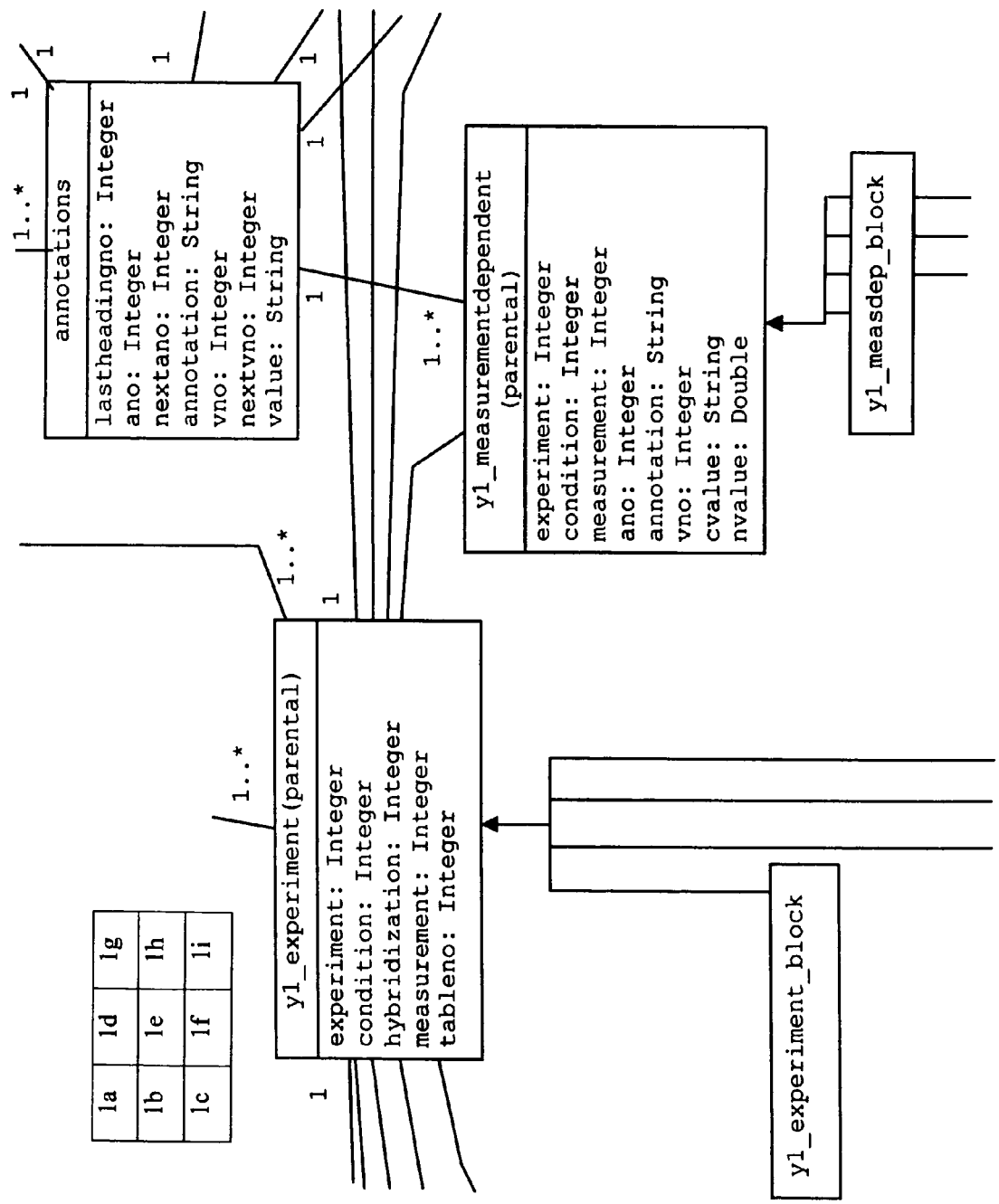
Figure 1F:
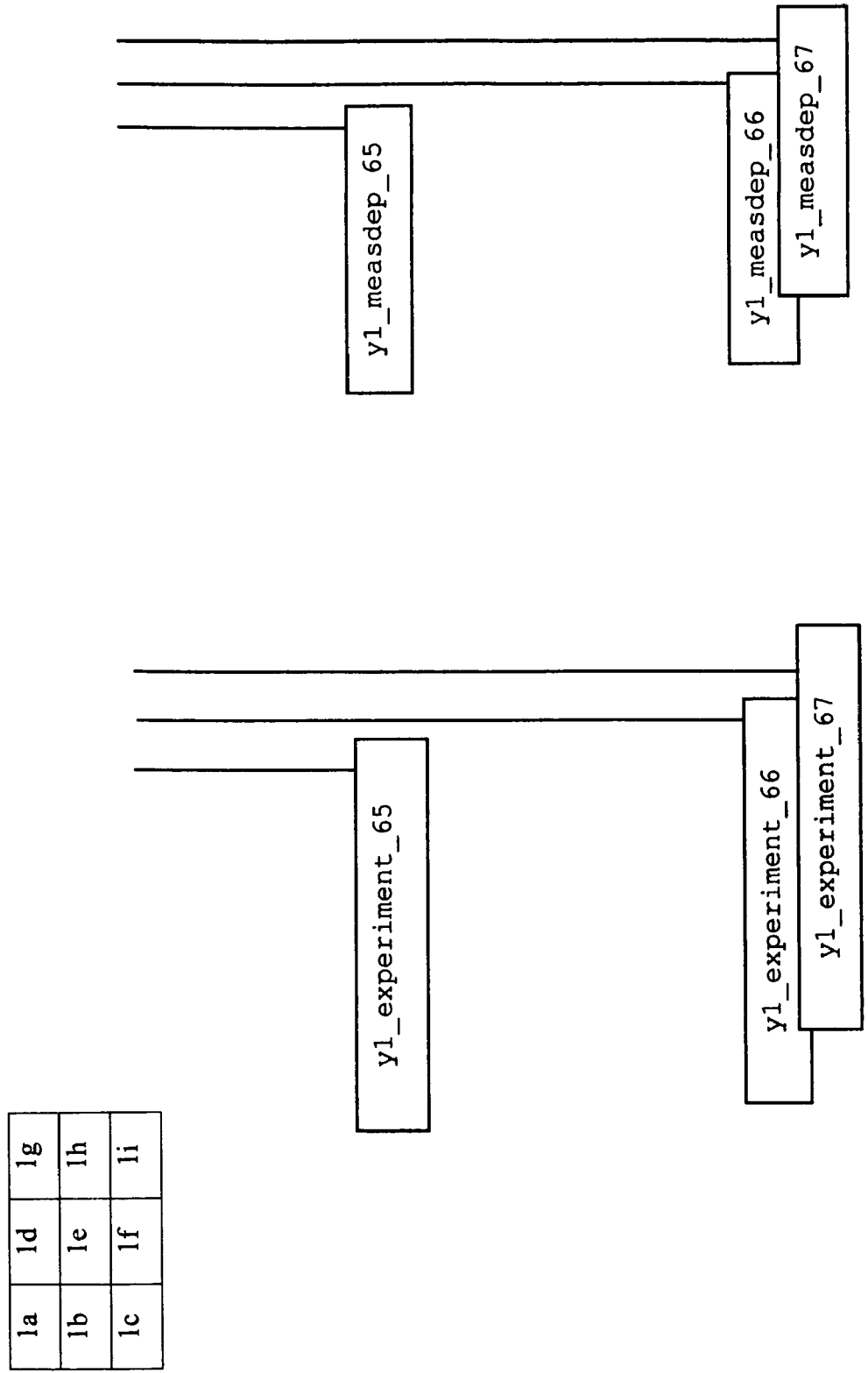
Figure 1G:
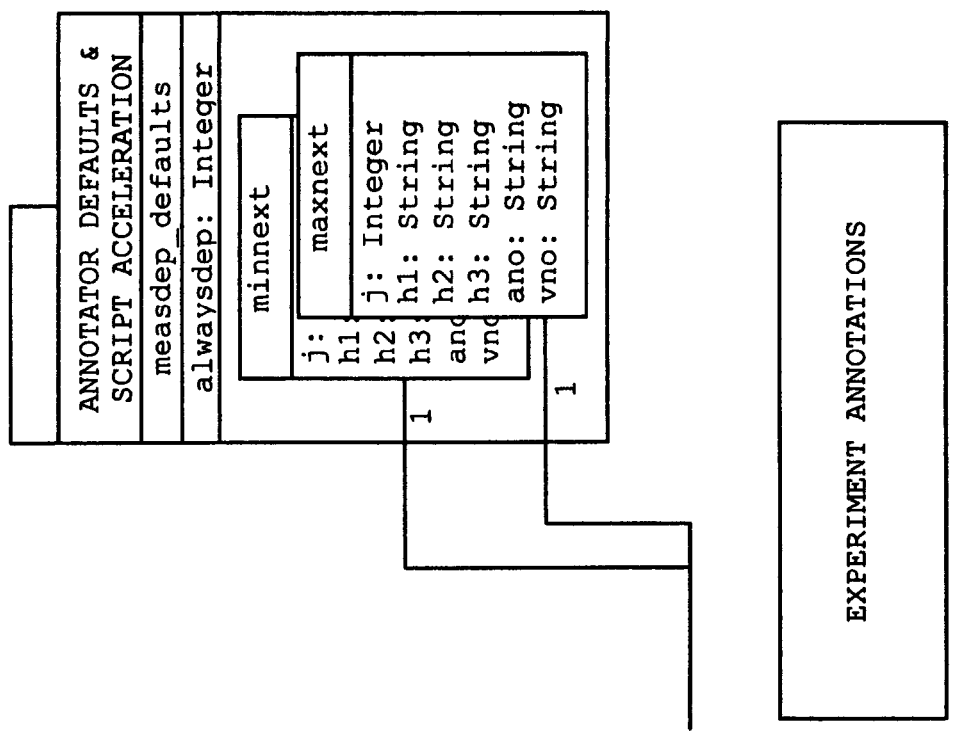
Figure 1H:
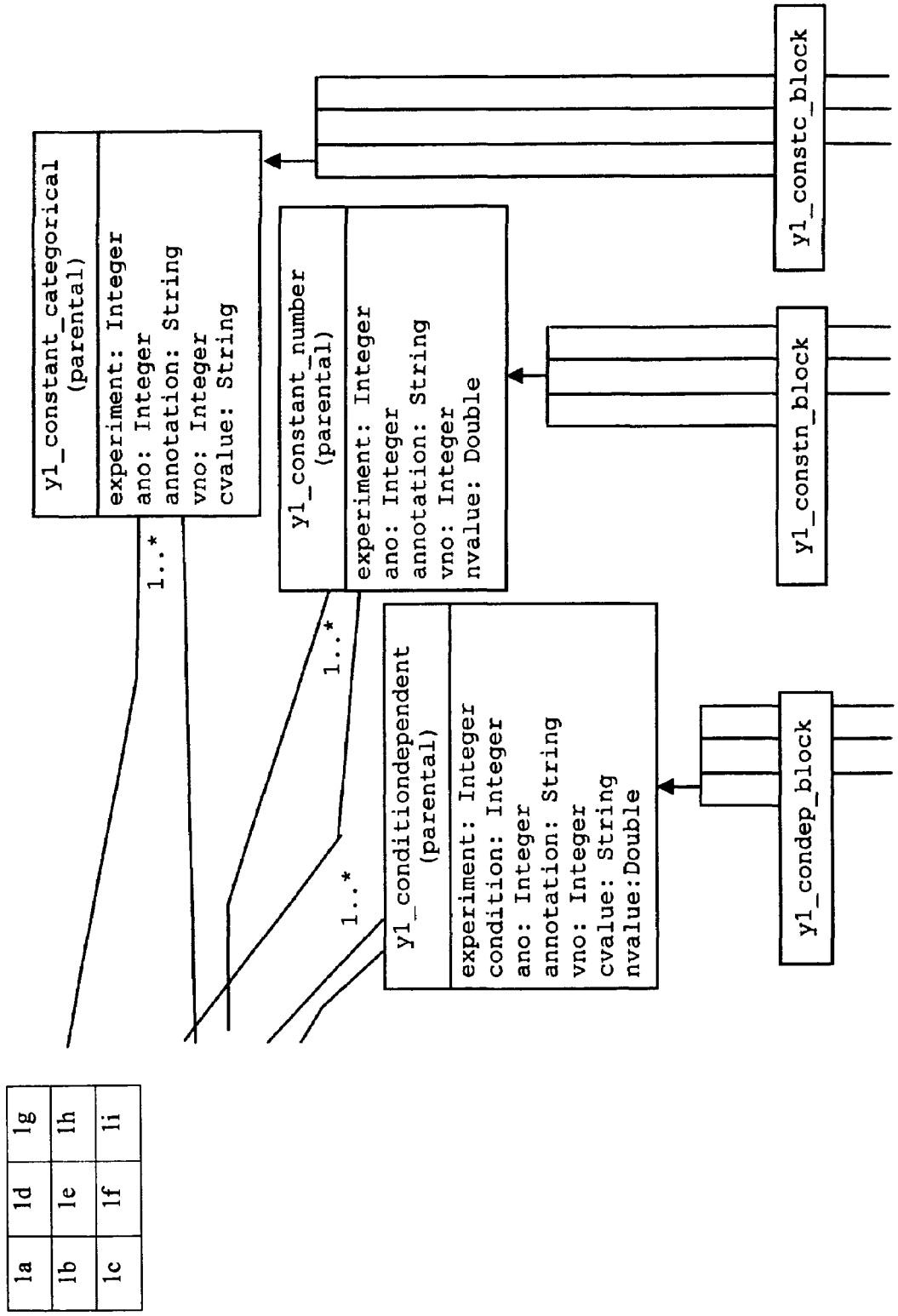
Figure 1I:
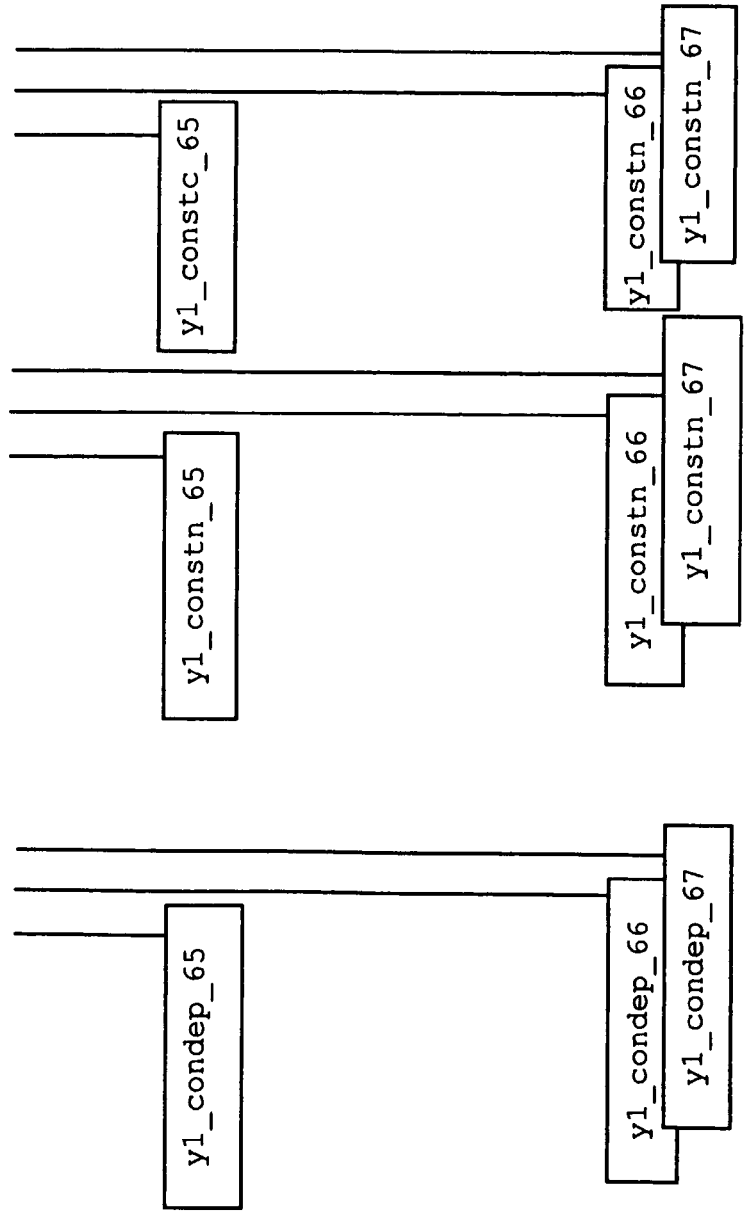

A hybridisation yields a huge amount of uniform data comprising, in one example, two intensities and two background values per gene or EST (being spotted in duplicate). Performance considerations would suggest hybridisation-wise storage in tab delimited files or array tuples in a database, dispensing with selective retrieval of particular values but allowing the fast access of whole hybridisations. Specified subsets of spots are neither easily accessible in a hybridisation data file nor in an array. However it should be possible to selectively retrieve intensities above a certain threshold or within a specified interval, thus it is necessary to store the values for every gene/EST as separate tuples in a database relation. In this form indices can be calculated to perform fast score-dependent queries utilizing the database capability of b-tree search. When in future hybridisation databases are too large to be loaded into computer memory, it will become necessary to perform tuple selections as well as simple calculations on the database level before loading compressed results into the memory for visualization.

The signal intensity obtained from the experimental apparatus, such as the microarray, should be preferably stored in raw form rather than as processed values as the processing algorithms for the signal intensity change rapidly. Therefore, any analysis should start with raw signal intensities and subsequently perform processing steps like normalization of the signal intensity data and filtering of the normalised data on the fly. The hybridisation on the microarray yields a simple although very large list of intensity values and background values for every spot on the microarray. These intensity values and background values could be stored in records or in so-called 'binary large objects' inside the database storage or in flat file format storage outside the database storage. However in such a case, it would not be possible to select subsets of data passing criteria like intensity thresholds or to perform simple calculations on the database level. Such calculations may be necessary in the future in order to normalize the vast datasets of signal intensity and background intensity data obtained and to extract from the dataset normalized data when the datasets do not fit into computer memory. Thus it is advantageous to store suggesting storage of intensity data in database tables. The system should be flexible enough to store signal and background intensity data stemming from both mono-channel (radioactive label) and multi-channel (fluorescent label) hybridisations.

Signal intensity data obtained by radioactive labelling do not represent the same quantities as the corresponding values obtained from fluorescent labelling. An example will serve to illustrate this. The absolute signal intensity values obtained from radioactive labelling are proportional to the amount of mRNA molecules in the target. The low value of absolute signal intensity value obtained from fluorescent labelling for a particular channel may result either from a low mRNA concentration in this channel or because the binding sites on the array are taken up by high amounts of differently labelled mRNA. Therefore pre-processing algorithms should be able to recognize the difference between the signal intensity values and automatically apply suitable methods such as normalization of the signal intensity values to correct this difference.

Gene annotations may consist of clone numbers, accession numbers and different kinds of entries describing the spotted sequence or the encoded protein like chromosomal location, enzyme categorization number or protein structure. As an example, identifiers serving as a key to connect to databases containing gene information, short variable length free text descriptions of the protein and its functional category and the spot location are included. Moreover it is advantageous to explicitly keep control of the array the spot is located on, provided that the spot set comprises more than one array and each of them has been hybridised separately.

Because complex sequence annotations or enzyme properties are found in linked gene databases, the gene annotations may be stored in only one relation containing attributes for the above values, and every spotted element (gene or EST) can be described by one tuple.

Experimental annotations comprise the description of environmental conditions, genotype, patient data, information about surgery, type of tissue (incl. estimated degree of contamination by other cell types), the sampling method and annotations related to hybridisation protocol, properties of the individual array or imaging process, to give some examples. They fall into the two realms of 1. Organism-specific annotations resembling the need of the specific research area such as e.g. 'transgene' and 'growth phase' for yeast or 'tumour type' and 'metastasis location' for human biopsies.
2. Common annotations that are useful for all fields of interest. These technique-related properties like array characteristics, description of labelling, hybridisation and washing conditions or detection of the signals are annotated by all the users.

Experimental annotations are set up by the biologists working in the field. They tend to grow with every new type of experiment performed. To account for this, an implementation of any concept will be useless if it does not enable easy and quick addition of new annotations or the completion of values for already defined annotations without altering the database scheme and the analysis algorithms. If an annotating experimenter finds something he or she forgot to define before uploading an experiment, the database should have the flexibility to easily and quickly incorporate a new annotation or value.

Gene and experimental annotations taken together sum up to less than 0.35% storage space of the yeast database (May 2000). Since the share of data entered directly by human beings as annotators may in any case have a size far too small to be relevant for query performance, flexibility is a time saving aspect related to experimental annotations.

For the conceptualisation of structures for data storage one might prefer formats supporting a wider range of analytical access to the data than others. Let the experimental annotations, though ordered into various categories and subcategories, be text fields containing free text description of the annotation value, e.g. the yeast specific annotation growth phase has a value: 'exponential'.

From researchers querying sequence databases in a high throughput manner, one can learn that there are severe problems like misspelling, different words having the same meaning, various types of abbreviations, making it hard to analyse the contents of a text field for a high number of datasets. On the other hand, one would expect the number of tuples (hybridisations/multi-conditional experiments) of a public expression database, once established, to grow quite fast. Researchers might cluster these tuples by the expression behaviour of a set of genes and would want to know which growth conditions, experimental settings, genotypes or environmental conditions of the organism corresponded to a particular cluster. In other words: Which properties are common for hybridisations that share similar expression patterns? This question cannot be answered by visual inspection alone when looking on hundreds of hybridisations with huge numbers of sample properties. Sample descriptions are favourable that enable inclusion of these descriptions into the process of analysis by algorithms. To make them accessible to statistical analysis, the values of an experimental annotation should be directly comparable among the datasets. If we, for example, let the above annotation 'growth phase' be an enumeration type variable comprising the defined values 'exponential', 'stationary' and 'pseudo-hyphal', the occurrence of the value 'exponential' can be counted within the cluster and compared with its overall occurrence to determine if it is characteristic (either over- or underrepresented) for the cluster. Prerequisite is that the annotation values are enumerable. Apart from enumeration type annotations already mentioned, floating point numbers can be made enumerable by mapping them to a set of bins, e.g. in a way that each bin covers an equally spaced range of values or in another manner that seems suitable for the particular annotation in terms of biological relevance.

The implementation of the database according to the invention works now for 33 yeast specific, 70 arabidopsis specific, 54 human tumour specific, 41 trypanosoma specific, and 76 common (technical) highly categorized experimental annotations. These were set up by biologists working in these fields enabling statistical analysis of the descriptions of nearly 1700 hybridisations stored in a PostgreSQL database. The following more practical aspects deal with the realization of such a database for a multi-user setting.

The invention provides a storage concept for unified analytical access to microarray experiments from different fields of research, an instance of which is a field-specific (organism-specific) database. Although these databases adopt different ontologies for experiment annotation, they can be accessed by the very same analysis algorithms. They are designed to be used by the people who generate the data. To meet the requirements of these users, they have to allow for multi-user access including safe management of simultaneous write access, short waiting periods and privacy (protection against unauthorized access).

Database Management Systems (DBMS) capable of the administration of more than one version of a database at the same time (like Oracle or PostgreSQL) and protect integrity of the stored data by transactions. Transactions give databases an all-or-nothing capability when making modifications. A transaction can comprise one or multiple queries with every of the performed changes becoming valid upon successful execution of the whole transaction and none of them in case of an error. At the same time all other users are insulated from seeing the partially committed transaction until the very moment of commitment, preventing database consistency from being damaged by simultaneous write access. Although transaction-based database management slows down access performance, it is preferable to use a transaction based DBMS.

Although the choice of a transaction-based DBMS ensures a great amount of safety for the data, there is no way to guarantee absolute security. In case of a disk head crash or failure in a server's power supply while updating important system catalogues it may well be that the integrity of all the databases managed by the server is destroyed at the same time. In such a case it is possible to restore the status of the last night for the whole database system from tape backup.

In case of accidentally deleting hybridisations from a single database it would be inappropriate to reset the whole system to the state of the night before. To be prepared for such a case, the invention provides for dumps to be performed separately for each database overnight. The dumps consist of SQL queries that can be used to restore data subsets from a whole database down to a single tuple of a particular table. To ensure that data (which may be unpublished) cannot be altered nor read by unauthorized individuals, update and/or read permissions can be granted on any database table to a particular user. Granting such permissions to user groups rather than separately to each user is a common procedure to circumvent the necessity of changing permissions for each database table upon registration of a new user. In the implementation of the invention nearly all the relations inherit from few parental tables and are accessed via their parental table only. Permission inheritance enables the administrator to quickly grant e.g. read access to a new user by changing permissions for a few parental tables in place of dealing with many tables or user groups. However, the main reason for access via parental tables is to enable pooling of tuples from hybridisation tables into large blocks without syntax alteration of accessing queries.

Since the overall extent of data referring to gene descriptions and experimental annotations is minimal, performance considerations are related only to hybridisation intensities. It is already quite efficient to divide the entirety of spots into appropriate subsets related to the type of queries that are performed. Most of the analysis queries target genes rather than empty or control spots, so it is preferable to store at least the genes separately from the rest. In the embodiment the spots are kept in tables belonging to (and inheriting from) 5 different parental tables comprising:

genes (genes/ESTs—incl. housekeeping)
empty spots (no DNA has been spotted)
heterologous DNA (e.g. guide spots)
heterologous DNA with known concentration (external control spots for 'spiking', i.e. assaying standard RNA aliquots added before the labelling step)
reference spots (reserved for a novel category of control spots).

As already mentioned in above, fast querying of tuples is mediated by indices. If the above categories would contain the hybridisations stored so far as one big block table per category, adding a new hybridisation would be quite slow because of the time necessary for recomputing the indices. Because of this, every new hybridisation is inserted as 5 new separate relations, computing indices only for the new tuples.

However querying for certain values is slowed down by increasing number of separate tables, because there is no global index guiding the search immediately to the one containing the tuple. This structure, while enabling high performance for write/delete operations impedes a fast read access. In order to optimize both for writing and reading operations, write/delete hybridisations are indicated in separate tables, but read from large blocks, which are produced by over-night jobs that join those tables (hybridisations) that are not to be altered or deleted any more. Thus, computing of large indices is performed at times of low traffic (as an investment in query performance).

On a SUN E450 server under Solaris 2.7, a PostgreSQL 6.5.3 server process retrieves 2 consecutively uploaded hybridisations (comprising 6103 yeast genes in double spotting) out of 686 ones stored in separate tables on average in 85 seconds. The same query performs in 2.3 seconds, if the 686 hybridisations are assembled into one big table. Even to retrieve two out of 2251 hybridisations takes only 2.8 seconds when all hybridisations are en bloc.

While storing hybridisations into blocks includes alteration of the database structure (decreasing the number of tables), it remains totally insulated from and invisible to the accessing software (algorithmic layer). Since every access to the intensity tables is directed via one of the five parental tables listed above query syntax does not change with the assembly of a set of tables into one block. This one block will be a child of a specific parental table as were the collected tables, summarized within the new block.

To meet the requirements described above, the categorization of experimental annotations should be kept in definition tables rather than mapped to database structure itself. In the invention, annotations along with their defined values are stored in a definition table. Each annotation has a unique identification number. They are stored as a linked list including an attribute pointing to the ID of the annotation next in sequence. The ID serves as a key for querying the annotations, the defined sequence allows for a clear list structure facilitating the annotation process. The annotations are structured by a set of headings and subheadings with an arbitrary nesting depth, which are stored in a second table. The linked list structure enables adding of a new annotation at an arbitrary position by linking of the desired predecessor to a new element that points to the ID of the element following in the list. In a similar manner the whole set of defined values is numbered sequentially to enable rapid queries and stored by a linked list in the same table as the annotations. To prepare for the administration of experiments related to a new field of research, it is sufficient to generate an empty database with definition tables containing the up-to-date list of common annotations along with a new second half of both annotation definition and heading table containing the 'organism-specific' annotations for the new field of experiments. A growing number of already assembled definition lists facilitate the compilation of new ones by serving as templates for the description of similar experimental procedures.

As described in above, the annotation values should be categorized down to an enumerable level, either directly by creating an enumeration type annotation, or by storing a floating-point number. These numbers are stored along with a unit if this is required for a unique meaning/message of the value. These do not necessarily have to be non-integer. Discretizing numbers will be reasonable in cases where similar values are expected to have the very same meaning in terms of their biological impact and the probability of those equivalent values to match the very same number is low because of measurement errors. The implementation of the above concepts will now be described. Database specific tables will be first described before showing schemes of the tables related to multi-conditional experiments and hybridisations. The entirety of microarray data can be divided into the sections shown in Table 1. Each section is a subset of the one ahead of it in terms of hybridisation intensities, but comes along with a unique set of annotations:

TABLE 1

Database sections

| Section | Intensity Data | Annotations |
|---|---|---|
| Database | containing all data derived from/related to one particular field of research (organism) | definition of valid experiment annotations along with a set of valid values for each of these annotations |
| microarray family | data obtained from one array type comprising a defined set of genes/ESTs in a particular spotting scheme | gene annotations (spot location, brief description and keys relating to external databases) |
| multi-conditional experiment | set of measurements comprising two or more experimental conditions incl. one 'control' condition | experiment annotations common throughout the experiment (unchanged in all of the conditions) |
| experimental condition | consists of one or more hybridisations repeatedly performed under the very same conditions | condition dependent experimental annotations (e.g. the timepoints in a timecourse) |
| measurement (image) | one image, i.e. one channel in case of multi-channel data - consists of genes/ESTs, empty spots and different kinds of reference spots, all of which are spotted in duplicate (referred to as 'primary' and 'secondary' spots) | measurement dependent experiment annotations (e.g. labelling efficiency, individual array no., number of previously performed hybridisations on the individual array) |

The microarray databases are administered by a PostgreSQL database server process running on a SUN E450. Data are uploaded, annotated and analysed by scientists working in different fields of research using samples from different organisms. A separate database is created for each organism/field and endowed with particular definitions of experimental annotations appropriate for the attended sort of sample. FIGS. 1a to 1i show the overview scheme for a database structure according to the invention. Apart from the experiment annotation definition-tables, the figure shows two more relations occurring only once per database in the 'DATABASE MANAGEMENT'-box. The first relation stores archive flags reporting any write access to either tables or BLOBSs (binary large objects) for an overnight job producing a new backup of the database. It also holds the database's structure version and nesting depth of its annotation hierarchy. The second is a register of the microarray families within the database.

The definition of experimental annotations consists of a table listing the annotations along with enumeration type values, a table containing the 'annotation headings' which provide a hierarchy of topics categorizing the actual annotations, and one recording those annotations usually being measurement dependent. These are shown in Table 2:

TABLE 2

Definition of experiment annotations (table structure)

| Field | Type | Length |
|---|---|---|
| Table = annotations | | |
| lastheadingno | int4 | 4 |
| ano | int4 | 4 |
| nextano | int4 | 4 |

TABLE 2-continued

Definition of experiment annotations (table structure)

| Field | Type | Length |
|---|---|---|
| annotation | text | var |
| vno | int4 | 4 |
| nextvno | int4 | 4 |
| value | text | var |
| Table = annotationheadings | | |
| heading1no | int4 | 4 |
| heading1 | text | var |
| heading2no | int4 | 4 |
| heading2 | text | var |
| heading3no | int4 | 4 |
| heading3 | text | var |
| Table = measdep_defaults | | |
| alwaysdep | int4 | 4 |

The annotation headings show a nesting depth of 3 heading levels. Here the fourth level of the hierarchy comprises the annotations themselves, the fifth their annotation values. For the annotation of an experiment the nested headings and annotations are compiled into one HTML form by a web interface running on a client computer. To accelerate the recursive CGI script, starting and end points of blocks consisting of elements to be sequentially listed in the form (but not necessarily being sequentially numbered in the linked list), are precompiled into arrays and recorded after updating the definition tables as shown in Table 3:

TABLE 3

Script acceleration tables (table structure)

| Field | Type | Length |
|---|---|---|
| Table = minnext | | |
| j | text | var |
| h1 | text | var |
| h2 | text | var |
| h3 | text | var |
| ano | text | var |
| vno | text | var |
| Table = maxnext | | |
| j | int4 | 4 |
| h1 | text | var |
| h2 | text | var |
| h3 | text | var |

TABLE 3-continued

Script acceleration tables (table structure)

| Field | Type | Length |
|---|---|---|
| ano | text | var |
| vno | text | var |

Heading1 is the highest level of the annotation hierarchy followed by lower heading levels, annotations and values. For any number j of a hierarchy element, the number of its first child in the next lower level is recorded in the relation "minnext". Here, it is stored under the attribute depicting this next lower level. 'H1' to 'h3' take the numbers of elements in the three heading levels, 'ano' contains the annotation numbers and 'vno' the value numbers. Likewise, the number of the last child in the next lower level is recorded in the relation "maxnext".

An example will show how experiment annotation definitions may look like in practice. In the first part a list of common annotations is defined in Table 4. These common annotations are used commonly by yeast, arabidopsis and human cancer biopsies to describe the more technical part of the experiment.

TABLE 4

Definition of experimental annotations (table contents)

yeast=> select * from annotationheadings order by heading1no, heading2no, heading3no;

| heading1no | heading1 | heading2no | heading2 | heading3no | heading3 |
|---|---|---|---|---|---|
| 1 | common_annotations | 1 | array | 1 | — |
| 1 | common_annotations | 2 | hybridisation | 2 | RNA_preparation |
| 1 | common_annotations | 2 | hybridisation | 3 | labeling |
| 1 | common_annotations | 2 | hybridisation | 4 | hybridisation_conditions |
| 1 | common_annotations | 2 | hybridisation | 5 | stringency_wash |
| 1 | common_annotations | 2 | hybridisation | 6 | detection |
| 1 | common_annotations | 3 | sample | 7 | — |
| 1 | common_annotations | 4 | submission | 8 | — |
| 2 | organism_specific_annotations | 5 | genotype | 9 | — |
| . . . skipping . . . | | | | | | yeast=> select * from annotations order by lastheadingno, ano, vno;

| lastheadingno | ano | nextano | annotation | vno | nextvno | value |
|---|---|---|---|---|---|---|
| 1 | 1 | 2 | array_source | 10 | 11 | self_made |
| 1 | 1 | 2 | array_source | 11 | 12 | genome_systems |
| 1 | 1 | 2 | array_source | 12 | 13 | clontech |
| 1 | 1 | 2 | array_source | 13 | 14 | research_genetics |
| 1 | 2 | 3 | array_series | 0 | 0 | [ ] |
| 1 | 3 | 4 | array_individual | 0 | 0 | [ ] |
| 1 | 4 | 5 | array_support | 14 | 15 | nylon |
| 1 | 4 | 5 | array_support | 15 | 16 | polypropylene |
| 1 | 4 | 5 | array_support | 16 | 17 | glass |
| 1 | 5 | 6 | spotted_material | 17 | 18 | PCR |
| 1 | 5 | 6 | spotted_material | 18 | 19 | colonies |
| 1 | 5 | 6 | spotted_material | 19 | 20 | DNA-oligo |
| 1 | 5 | 6 | spotted_material | 20 | 21 | PNA-oligo |
| 1 | 6 | 7 | readfile | 0 | 0 | [ ] |
| 1 | 7 | 8 | array_hybridisation | 0 | 0 | [ ] |
| 2 | 8 | 9 | material_source | 21 | 22 | fresh |
| 2 | 8 | 9 | material_source | 22 | 23 | frozen |
| . . . skipping . . . | | | | | | |

The HTML output for an annotation input form compiled from values in Table 4 is shown in FIG. 2.

A database can comprise different sorts of microarrays. Each family represents a unique spotting scheme including genes or ESTs and reference spots. For a family referred to as 'y1' by the master table of the database yeast, there are 5 gene annotation tables corresponding to the categories mentioned above.

TABLE 5

Spot categories

| Category | table name |
| --- | --- |
| Genes | y1_genes |
| empty spots | y1_empty |
| heterologous DNA | y1_hetrl |
| heterologous DNA with known concentration | y1_hetkc |
| reference spots | y1_refgs |

All of these gene annotation tables share the same scheme as shown in Table 6:

TABLE 6

Gene annotations (table structure)
Table = y1_gene

| Field | Type | Length |
| --- | --- | --- |
| spotno | int4 | 4 |
| field | int4 | 4 |
| plate | int4 | 4 |
| letter | char | 1 |
| number | int4 | 4 |
| ext_link 7 | char | 7 |
| ex_link10 | char | 10 |
| partition | int4 | 4 |
| description | text | var |
| functional_catalogue | text | var |
| Indices:y1_genes_isn | | |
| y1_genes_if | | |
| y1_genes_ip | | |
| y1_genes_il | | |
| y1_genes_in | | |
| y1_genes_in7 | | |
| y1_genes_in10 | | |
| y1_genes_ipart | | |
| y1_genes_id | | |
| y1_genes_ifc | | |

An index has been computed for every attribute with the name of each index relation consisting of the family, the spot category and an abbreviation of the indexed attribute (attributes and their indexes are listed in the same sequence).

The attribute 'spotno' serves as a key connecting to the tables that contain hybridisation intensities. The attributes 'field', 'plate', 'letter' and 'number' correspond to the spot location on the array as well as to the DNA stock kept in micro-titre plates. Two fields of fix length ('ext_link7' and 'ext_link10') are reserved for keys linking to external databases and 'description' and 'functional_catalogue' contain a brief description of the protein and its function of variable form and size. Certain spot sets may have to be normalized separately. In such cases the partition of the spots is recorded by the attribute 'partition'.

There are two more tables belonging to an array family (see detailed scheme, also in 'DATABASE MANAGEMENT'). To stick to the example family 'y1' (comprehensive yeast filter), there is a table named 'y1' storing the number of multi-conditional experiments as well as the number of measurements in the family. Since each measurement is initially stored in a separate table and identified with a unique table number, their quantity is attributed as 'tables'. Generally, 'measurement 5' identifies the 5th measurement of a particular experiment, whereas 'tables'/'tableno' hold quantity/IDs of measurements on a family-wide scale (even when the initial tables have been merged into a block).

TABLE 7

Information about an array family (table structure)
Table = y1

| Field | Type | Length |
| --- | --- | --- |
| experiments | int4 | 4 |
| tables | int4 | 4 |
| i_filefomat | int4 | 4 |

The third attribute ('input file format') stores the version number of the script capable of reformatting an output file of a particular imaging software into the format of a database table. This MATLAB function exists in different versions enumerated sequentially for different imaging software types and spotting schemes.

The second table lists the multi-conditional experiments contained by the family.

TABLE 8

Experiments contained in an array family (table structure)
Table = y1_master

| Field | Type | Length |
| --- | --- | --- |
| experiments | int4 | 4 |
| ex_name | text | var |
| ex_table | int4 | 4 |
| conditions | int4 | 4 |
| condep-ano | text | var |
| Indices:y1_master_iex | | |
| y1_master_ien | | |
| y1_master_iet | | |
| y1_master_ico | | |
| y1_master_ica | | |

Each experiment is assigned a number and a name 'ex_table' links to the administration table for the hybridisation intensities as well as to the experimental annotations. For convenience in algorithm handling, the number of comprised conditions as well as the varied experimental parameters ('condition-dependent annotations') are redundantly included.

There may be an arbitrary number of multi-conditional experiments hybridised on a particular filter family. They may be time courses, variations of agent concentrations in culture media, comparisons of different genotypes just to give some examples, consisting of several experimental conditions which are intended to be directly comparable. To learn something from such a comparison not too many parameters should be altered among the conditions performed. Hence most of the experimental conditions are constant for the entire experiment, some are condition-dependent and some are measurement-dependent, i.e. they can take different values for each single measurement, e.g. the label incorporation rate. For fast annotation via the annotation input form, the data are required in the form of these three sets of annotations. For statistical analysis, they are needed hybridisation-wise. Redundancy caused by hybridisation-wise storage of the entire set of annotations would have little effect in terms of storage space or performance because these annotations are of negligible volume as discussed above. However, it was decided to store them in separate relations for convenient algorithm handling. Splitting up a uniform set of hybridisation-wise stored annotations into hybridisation-dependent, condition-dependent and constant annotations requires repeated value comparison, whereas the distribution of constant and condition-dependent annotations to each hybridisation is a trivial task.

Constant annotations are stored in two separate tables per multi-conditional experiment just to be more readable rather than for computational reasons. These tables are children of parental tables 'y1_constant_categoricalvalue' and 'y1_constant_number' respectively. The numbers within their names as well as the content of the field 'experiment' correspond to the according key in y1_master.

TABLE 9

Experimental annotations constant throughout the experiment (table structure)

| Field | Type | Length |
|---|---|---|
| Table = y1_constant_categoricalvalue 65 | | |
| experiment | int4 | 4 |
| ano | int4 | 4 |
| annotation | text | var |
| vno | int4 | 4 |
| cvalue | text | var |
| Table = y1_constant_number 65 | | |
| experiment | int4 | 4 |
| ano | int4 | 4 |
| annotation | text | var |
| vno | int4 | 4 |
| nvalue | float8 | 8 |

The first table of table 9 takes the enumeration type ('categorical') annotations, the second one those consisting of a number. This is reflected by the type of the attributes 'cvalue' and 'nvalue', which is the only difference among the above schemes. As a representative of intended redundancy both number ('ano') and name ('annotation') are enlisted for an annotation as well as for its value. Because of the small amount of storage space required for the annotations, this does not have major consequences for storage space or for performance. However, the redundancy might serve to reconstruct experimental annotations (which would be very time consuming to re-enter by hand) if an error occurs in the numbering of annotations or values. Redundant storage appears advisable here because as new kinds of experiments evolve, annotation definitions are under constant change.

For each condition in a multi-conditional experiment, there is a table like the one shown in table 9, which in our example, family y1 inherits from a parental relation y1_experiment. For the above experiment no. 65 it will be named y1_ex_65.

TABLE 10

Association of experiments, conditions and measurements (table structure)
Table = y1_experiment_65

| Field | Type | Length |
|---|---|---|
| experiment | int4 | 4 |
| condition | int4 | 4 |
| hybridization | int4 | 4 |
| measurement | int4 | 4 |
| tableno | text | var |

The field 'experiment' will contain an entry 65 as well for the entirety of tuples to identify the experiment in a family-wide context, since the experiment tables can be merged into big block relations as for the intensities. The comprised conditions have been studied by several repeatedly performed hybridisations which themselves consist of one (radioactive labelling, mono-channel) or more (multi-channel fluorescence data) measurements (frequently called channels or images). While 'measurement' identifies a measurement in the context of its particular experiment, 'tableno' holds its family-wide ID. Both remain unchanged when the initial tables are merged into a block.

The number of successfully performed hybridisations and measurements may vary among the conditions. As an example we show in table 11 the content of the above relation that outlines an experiment with radioactive (mono-channel) hybridisations:

TABLE 11

Association of experiments, conditions and measurement (table content)
yeast=> select * from y1_experiment_65 order by tableno,

| experiment | condition | hydbridization | measurement | tableno |
|---|---|---|---|---|
| 65 | 0 | 1 | 1 | 576 |
| 65 | 0 | 2 | 2 | 577 |
| 65 | 0 | 3 | 3 | 578 |
| 65 | 1 | 4 | 4 | 579 |
| 65 | 1 | 5 | 5 | 580 |
| 65 | 1 | 6 | 6 | 581 |
| 65 | 2 | 7 | 7 | 582 |
| 65 | 2 | 8 | 8 | 583 |
| 65 | 2 | 9 | 9 | 584 |
| 65 | 2 | 10 | 10 | 585 |
| 65 | 2 | 11 | 11 | 586 |
| 65 | 3 | 12 | 12 | 587 |
| 65 | 3 | 13 | 13 | 588 |
| 65 | 3 | 14 | 14 | 589 |
| 65 | 3 | 15 | 15 | 590 |
| 65 | 3 | 16 | 16 | 591 |
| (16 rows) | | | | |

The control condition is identified by a zero whereas numbering of hybridisations and measurements starts at one. While in the above case the measurement IDs correspond to those of the hybridisations, they are different in multi-channel experiments where each hybridisation comprises more than one measurement belonging to different conditions. Whereas the sequence recorded in 'measurement' is due to the experiment (with the first one of a hybridization usually being the 'red' channel), the purpose of 'tableno' is rather technical. It simply corresponds to the order in which they were uploaded into the database, being a unique ID.

The condition-dependent annotations describing experiment no. 65 are stored in y1_conditiondependent_65 as illustrated in the following table 12.

TABLE 12

Condition dependent annotations (table structure)
Table = y1_conditiondependent_65

| Field | Type | Length |
|---|---|---|
| experiment | int4 | 4 |
| condition | int4 | 4 |
| ano | int4 | 4 |
| annotation | text | var |
| vno | int4 | 4 |
| cvalue | text | var |
| nvalue | float8 | 8 |

It shows the same structure as for the constant annotations, except for including both numbers (stored in 'nvalue') and enumeration type values (in 'cvalue') into one table. Moreover it contains an additional attribute accounting for the condition. Enumeration of conditions starts at zero for the control condition.

TABLE 13

Condition dependent annotations (table content)
yeast=> select * from y1_conditionsdependent_65 order by ano, condition, vno;

| experiment | condition | anno | annotation | vno | cvalue | nvalue |
|---|---|---|---|---|---|---|
| 65 | 0 | 1035 | strain | 1091 | 3E2 | NaN |
| 65 | 1 | 1035 | strain | 1091 | 3E2 | NaN |
| 65 | 2 | 1035 | strain | 1092 | 702 | NaN |
| 65 | 3 | 1035 | strain | 1092 | 702 | NaN |
| 65 | 0 | 1037 | genetic_variation | 1100 | WT | NaN |
| 65 | 1 | 1037 | genetic_variation | 1100 | WT | NaN |
| 65 | 2 | 1037 | genetic_variation | 1099 | inducible_promoter | NaN |
| 65 | 3 | 1037 | genetic_variation | 1099 | inducible_promoter | NaN |
| 65 | 0 | 1038 | transgene | 0 | *** | 0 |
| 65 | 1 | 1038 | transgene | 0 | *** | 0 |
| 65 | 2 | 1038 | transgene | 0 | *** | 4111 |
| 65 | 3 | 1038 | transgene | 0 | *** | 4111 |
| 65 | 0 | 1049 | glucose | 0 | *** | 2 |
| 65 | 1 | 1049 | glucose | 0 | *** | 0 |
| 65 | 2 | 1049 | glucose | 0 | *** | 2 |
| 65 | 3 | 1049 | glucose | 0 | *** | 0 |
| 65 | 0 | 1050 | galactose | 0 | *** | 0 |
| 65 | 1 | 1050 | galactose | 0 | *** | 2 |
| 65 | 2 | 1050 | galactose | 0 | *** | 0 |
| 65 | 3 | 1050 | galactose | 0 | *** | 2 |

(20 rows)

In this particular experiment both the genotype of the yeast cells and the carbon source of their medium had been varied. For enumeration type annotations like 'strain', a valid value number ('vno') is listed but the field 'nvalue' contains 'not-a-number'. Conversely, floating point number annotations like 'transgene' or 'glucose' have 'valueno' 0 and a dummy entry for 'cvalue', but a meaningful 'nvalue' (namely the floating point value, which happens to be always a natural number in the above table).

Like in the above tables, a field is included that denotes the experiment number for every tuple for identification in block context. The corresponding parental tables (in the above case 'y1_conditiondependent' is the name of the parent table) are themselves empty but mediate queries on all of their children. This means that the query syntax given on top of the table list is never used. Instead all the algorithms involved would query this table by an instruction of the form:

yeast=>select * from y1_conditiondependent* where
    ex=65 order by ano, condition, vno;

resulting in the very same list.

As listed in the administration table for experiment 65 (see table 11), the third measurement of the last condition is hybridisation number 589. The corresponding intensities are stored in 5 separate tables as explained above and are accessed via the parental tables 'y1_g', 'y1_e', 'y1_h', 'y1_k' and 'y1_r'. The tables are of a uniform structure that they inherited from their uniform parental tables, one example being:

TABLE 14

Hybridization intensities (table structure)
Table = y1_g_589

| Field | Type | Length |
|---|---|---|
| tableno | int4 | 4 |
| sporno | int4 | 4 |
| prim | float8 | 8 |
| sec | float8 | 8 |
| prim_bkg | float8 | 8 |
| sec_bkg | float8 | 8 |
| Indices:y1_g_589_ipr | | |
| y1_g_589_ise | | |
| y1_g_589_isn | | |

Since this kind of tables is also accessed by querying the parental table, 'tableno' mediates identification in block context, linking to the administration table (y1_experiment). 'Spotno' identifies the spot, corresponding to the identically named attribute of the gene annotation table 'y1_genes' (3.2.1). In the tables 'y1_e_589', 'y1_h_589', 'y1_k_589' and 'y1_r_589' this attribute corresponds to the 'spotno' in 'y1_empty', 'y1_hetrl', 'y1_hetkc' and 'y1_refgs', respectively. The remaining attributes contain the hybridisation intensities. Each gene or EST has been spotted in duplicate resulting in two intensities ('prim' and 'sec') per hybridisation. The last two attributes are intended to take a local background value that is delivered by most of the imaging software packages. Three indices have been computed. 'y1_g_589ipr' and 'y1_g_589_ise' facilitate the search for specific hybridisation intensities ('pr' and 'se' for primary and secondary spots), 'y1_g_589_isn' querying certain spot numbers.

Many imaging software packages yield more than one intensity score and background per spot. Commonly, they provide differently calculated intensities (e.g. pixel mean, median), background intensities and various kinds of quality or reliability measures. From these, the contents of the above tables are either chosen or calculated as a starting point for standardized analysis in the process of database upload.

As experiments are analysed and valued, hybridisations are deleted e.g. for bad signal quality, written into another context or kept in the experiments and conditions into which they were uploaded. When a set of hybridisations is no longer to be altered, it is solidified, i.e. written into large block tables over night, as mentioned in above. The separation into the 5 spot categories is kept, thus resulting in 5 block tables. Tuples of the above table will go e.g. into y1_g_block1.

TABLE 15

Hybridization intensities in a block (table structure)
Table = y1_g_block1

| Field | Type | Length |
|---|---|---|
| tableno | int4 | 4 |
| sporno | int4 | 4 |
| prim | float8 | 8 |
| sec | float8 | 8 |
| prim_bkg | float8 | 8 |
| sec_bkg | float8 | 8 |
| Indices:y1_g_block1_ipr | | |
| y1_g_block1_ise | | |
| y1_g_block1_isn | | |
| y1_g_block1_itn | | |

These tables have exactly the same structure as the normal hybridisation tables. The only difference is that an index was computed for the table numbers (named 'y1_g_block1_itn') enabling rapid hybridisation wise retrieval of the tuples from the block. Such a block was tested with up to 538 hybridisations of the y1 type (comprising 6103 genes), speeding up retrieval of an entire multi-conditional experiment up to 15fold compared to the un-solidified version depending on how many hybridisations are comprised, and on its position in the database.

For measurement-dependent annotations, structures mentioned for the condition-dependent annotations (table 12) apply as well. The table 'y1_measurementdependent_65'' containing the measurement-dependent annotations of multi-conditional experiment 65 inherits from the table y1_measurementdependent and has the same structure as the table y1_conditiondependent_65 except for one additional attribute 'measurement', which is related to the intensity tables by relation y1_experiment_65. 'Condition' is related to 'measurement' here as well to secure this important information by repeated storage.

TABLE 16

Measurement dependent annotations (table structure)
Table = y1_measurementdependent_65

| Field | Type | Length |
|---|---|---|
| experiment | int4 | 4 |
| condition | int4 | 4 |
| measurement | int4 | 4 |
| ano | int4 | 4 |
| annotation | text | var |
| vno | int4 | 4 |
| cvalue | text | var |
| nvalue | float8 | 8 |

Although all defined annotations have to be annotated for a multi-conditional experiment, their distribution among the hybridisation-dependent, condition-dependent and constant database relations may vary from experiment to experiment. Annotation starts by choosing the annotations that shall become measurement-dependent and thereafter assigning a value to each of those annotations for each measurement. Thereafter, the condition-dependent annotations are selected and annotated before the remaining constant annotations are entered. The annotation process is mediated by an annotation input form using a web interface such that annotation can be performed from remote sites by annotators, enabling annotation even before uploading of intensities, re-editing of assigned values and copy from similar experiments to save the annotators from re-entering identical values.

The database was designed to be charged and queried by the experimenters themselves using algorithms, which mediate upload and annotation of experiments, as well as data analysis. The invention comprises C, Perl and MATLAB functions.

Experiments can be annotated from remote by the experimenters themselves using the annotation input form. The generation of the annotation input form is described above. Annotation appears to be a time-consuming process, if hundreds of experimental parameters have to be entered for each single measurement. For this reason, the possibility is provided to select annotations that are constant or condition-dependent as defined above and that have to be entered only once, in contrast to measurement-dependent annotations. Furthermore, it is possible to copy the whole set of annotations from a similar experiment and edit only the differing ones. It is likely that only few parameters are varied per condition, so the majority of the annotations is constant throughout the experiment. Among these, the majority are constant for more than one particular experiment. This reflects more or less constant execution of the same protocols for e.g. hybridisation and washing.

Figure 3A:
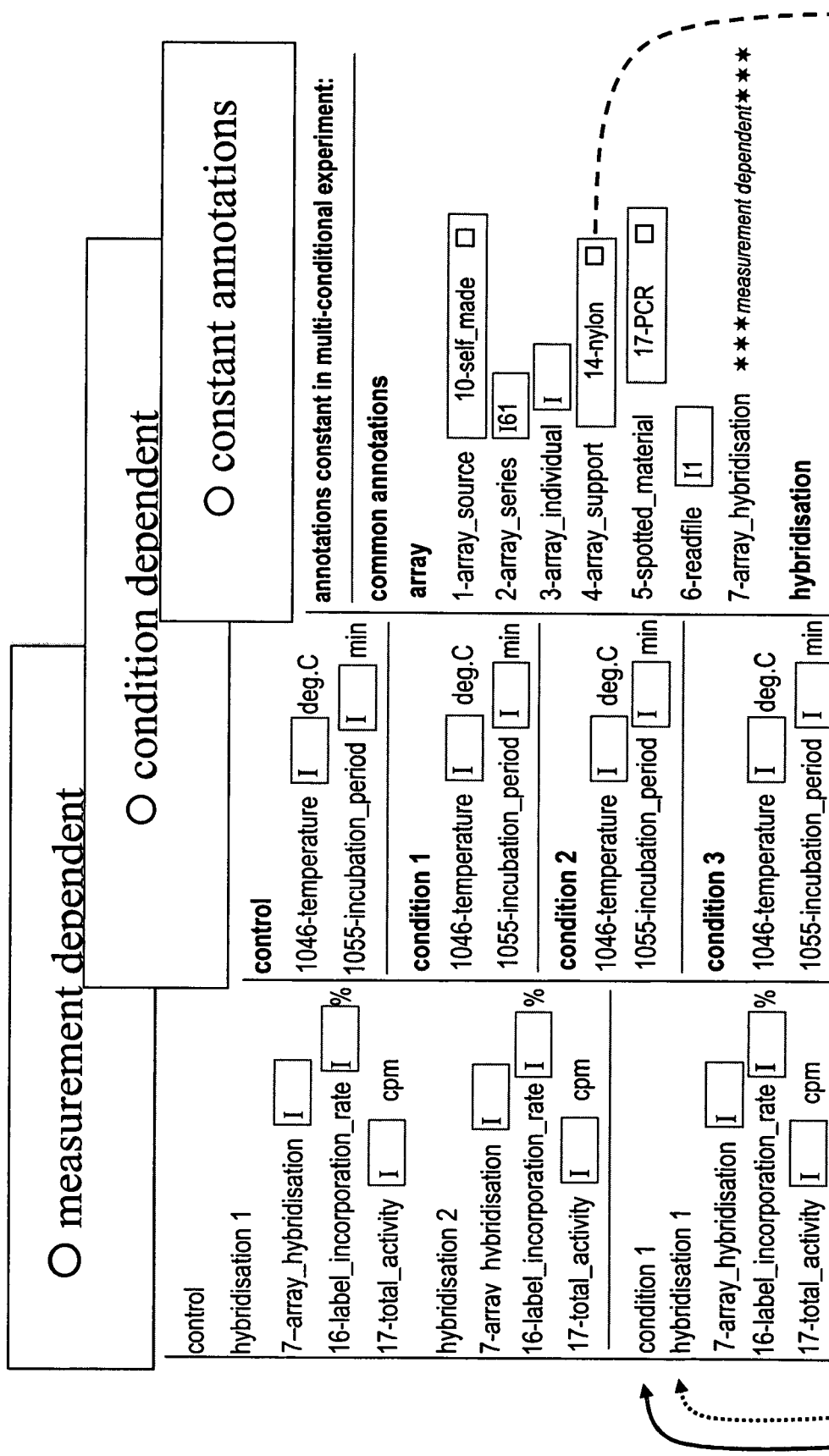
FIG. 3 shows the annotation process.
Figure 3B:
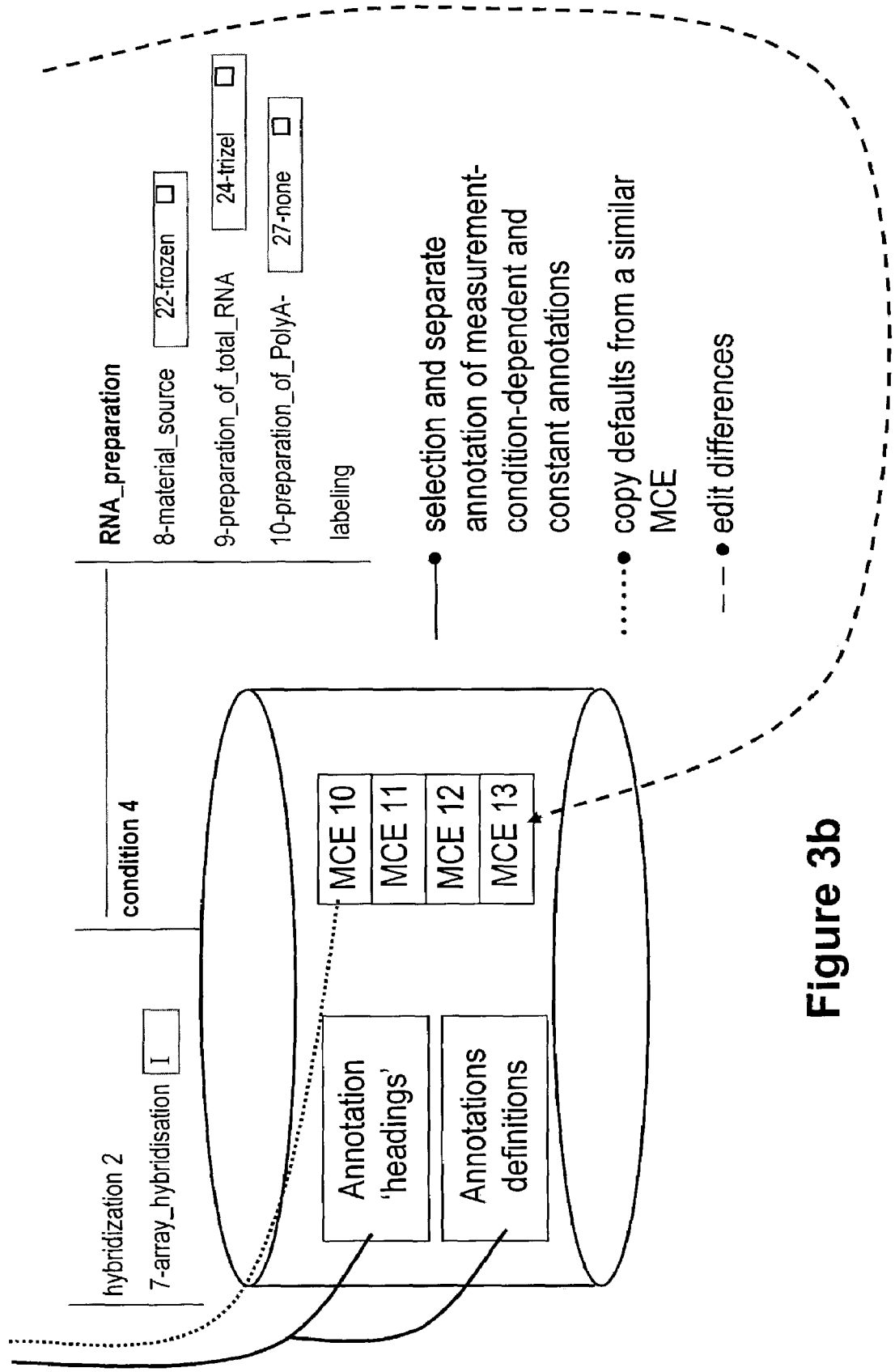

The annotation process is sketched in FIG. 3. It is possible to enter detailed descriptions (111 annotations) of large multiconditional experiments (24 measurements) in less than 15 minutes using the invention. In the invention, pre-processing starts with normalization of raw signal intensities. The normalization is based on robust affine-linear regression of one measurement versus a control measurement (see below). The performance may be judged from the scatterplot of the raw data (measurement versus control measurement). In this plot, a regression line represents the multiplicative distortion and additive offset determined by the fitting algorithm. The performance of the fit is visible in how well the regression line matches the central dense parts of the cloud. Furthermore it can be observed, which properties of the raw data led to an eventual sub-optimal result. The scale of the plot can be switched between linear and double-logarithmic. In log scale the regression line appears as a curve—the curvature of which depends on the additive offset between the two measurements. Two algorithms as described in Beiβbarth et al. (2000) and Fellenberg et al. (2001) are used. For both, the set of trusted spots of unvaried expression taken into account for fitting can be specified (housekeeping genes, external controls, or entire set). The invention discriminates between mono- and multi-channel experiments. For the former, each measurement is normalized versus the genewise median of the hybridisations for the control condition, resulting in absolute intensities. For the latter, the channel belonging to the control condition serves to normalize the other channel(s) of the same hybridisation, resulting in intensity ratios. For many arrays and experiments, the majority of genes spotted on the array is not expressed to a measurable amount. While displaying notable ratios due to measurement fluctuations, they can be eliminated by means of an intensity filter. To compute intensity levels from multi-channel ratios, these ratios are multiplied with an average control measurement, being the genewise median of the absolute values of the control channels.

Apart from intensity and ratio filters, reproducibility measures (Beiβbarth et al., 2000) are applied to extract genes that are reproducibly up- or down regulated. These measures integrate repeatedly performed measurements for the same experimental condition. In addition, they are plotted versus the average intensity level and ratio as a measure for quality control.

Figure 4:
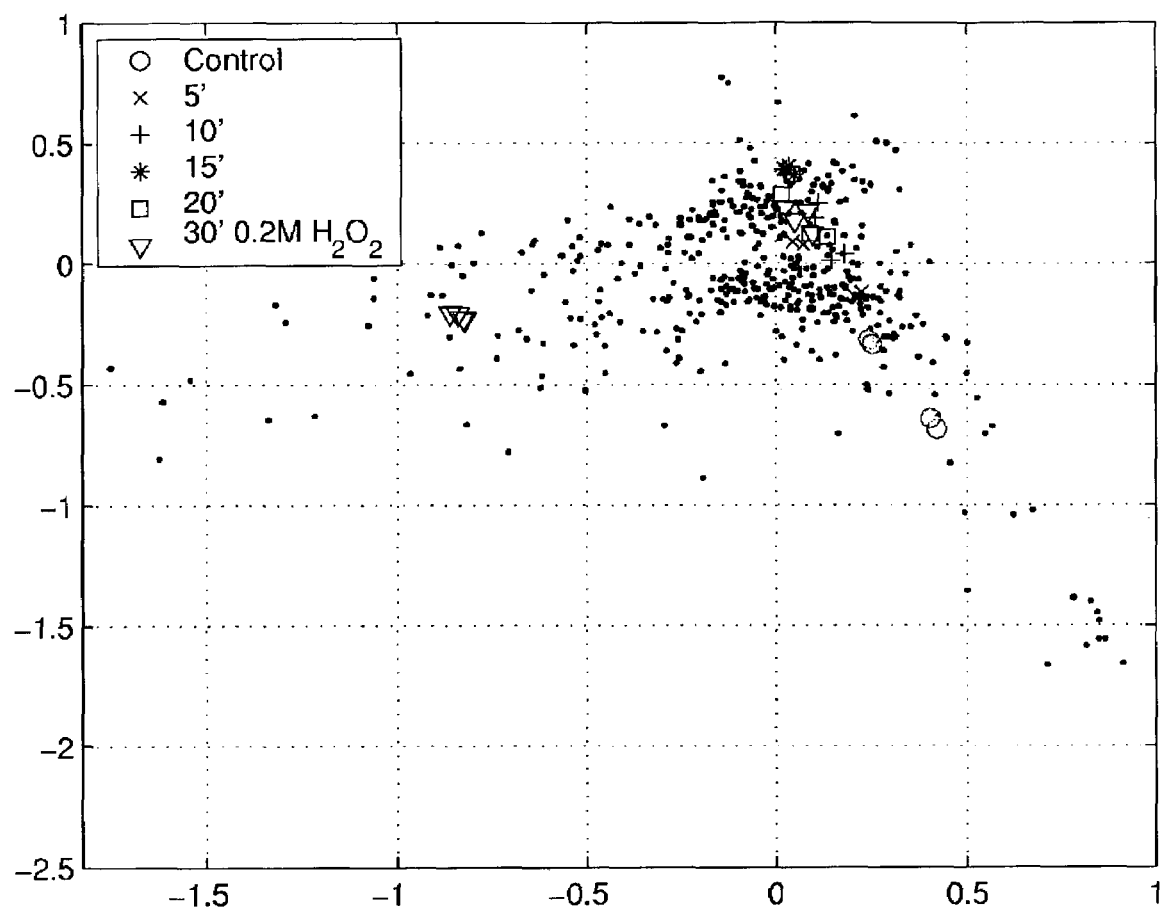
FIG. 4 shows a cluster of microarray hybridisations.

Statistical analysis techniques used to analyse results include hierarchical clustering (Eisen et al., 1998), correspondence analysis (Fellenberg et al., 2001), and statistical analysis of experiment annotations for arbitrary sets of hybridisations, e.g. those clustered by similar expression profiles. Comparison of different visualizations of a dataset are facilitated by highlighting data points which have been selected in another plot. It is also possible to mark all genes bearing a certain keyword like 'cell-cycle' in their gene annotation or to import multiple sets of gene tags from text lists. In the correspondence analysis plot, several disjoint gene sets can be visualized by different colour, e.g. to highlight different functional categories or to mark interesting clusters of genes. For the latter, gene sets can be selected by encircling them by mouse clicks. Expression profiles of marked genes can be displayed in a parallel coordinate plot. In the same manner clusters of measurements can be selected and plotted. Moreover, they can be automatically scanned for significant experiment annotation values. For each value of every annotation, instances of occurrence are counted. For a particular value its frequency in the cluster is determined as the number of its occurrences in the cluster divided by the number of measurements in the cluster. Comparison to its frequency in the whole set of measurements under study reveals whether it is over- or underrepresented in the cluster. An example is shown in FIG. 4.

A time course has been recorded for wild type *s. cerevisiae* cells under oxidative stress by 0.2 M hydrogen peroxide. Data have been pre-processed and visualized by correspondence analysis. The plot comprises both genes and measurements. The genes are depicted as black dots. Measurements are shown as squares and can be colour-coded according to the experimental condition they belong to. There is one outlying cluster of measurements belonging to the 30-minutes time point, whereas other measurements of the very same condition are located in a distant area, clustering with other time points. Selecting these outliers, searching for at least 2 fold over- or under-represented annotation values results in values belonging to only 8 out of 111 annotations (see FIG. 5).

The first two annotations listed in FIG. 5 provide the information that the entire cluster was hybridised on array individual 6 which is the only one stemming from array series (i.e. production batch) 59, whereas all other arrays were of series 61. From other experiments, we generally observed sufficient comparability among arrays of the same production series, whereas arrays of different batches could not be directly compared.

Sometimes, especially with higher numbers of measurements, it is desirable to aggregate values for annotations of continuous range (see no.16 and 17 in FIG. 5). 'Label incorporation rate' may thus be discretized into e.g. low, medium and high values. The invention provides methods enabling discretization of annotation ranges into a chosen number of bins due to their particular distribution or by expert knowledge.

The invention allows information from heterogeneous experiments to be stored in databases of similar structure so that the same algorithms for analysis can be applied. Thus, all algorithms described above have been extensively tested. Currently we have 33 yeast specific (MIAME compliant**), 54 human tumor specific, 71 arabidopsis specific (MIAME compliant), 41 trypanosome specific, 20 neurospora specific and 78 common, technical, MIAME compliant experiment annotations. Compliance with standards such as e.g. those proposed by EBI (MIAME) is independent from our storage scheme. The annotator and/or the experimenter defining the annotations decides about standard compliance and level of detail. The entire descriptions of all hybridisations stored in our databases can be analysed statistically. There are currently more than 1700 hybridisations kept in 12 databases. They belong to the above 5 fields of research and comprise both radioactive-label and multi-channel experiments.

The storage system provides an unprecedented level of detail for experiment description captured in categorical and continuous variables. For data entry, this ensures completeness of experiment annotation, i.e, a level of completeness exceeding minimal standards. For analysis, it provides the capability to include experiment information as additional variables, i.e. to study it by means of multivariate statistics. Additional attributes or additional allowed values for existing attributes can easily be added without changing the database structure.

Previously published microarray database concepts have focused on the ability to include intensity data from different platforms and to make these comparable (Aach et al., 2000; Brazma et al., 2000). Some projects have started to develop controlled vocabulary for experiment description (e.g., ArrayExpress, RAD and GEO). However, little effort has been made to date to categorize the descriptions down to minute detail and make them amenable to analysis. The invention has provided databases and analysis tools for data from different areas of research (i.e. experiments with yeast, arabidopsis, *T. brucei, N. crassa* and human cancer samples), obtained by different platforms (radioactive hybridisation to nylon or polypropylene membranes and fluorescent hybridisation to glass slides), and by means of different imaging software.

Experiment annotation is web-based to ensure that any experiment can be annotated from remote by the experimenters themselves. Efforts for annotating experiments are minimized. Data analysis comprises pre-processing, e.g. different methods for normalization, the performance of which can be visually checked, quality control plots, and gene extraction by intensity, ratio and reproducibility thresholds (Beiβbarth et al., 2000; Fellenberg et al., 2001). High-level analysis techniques include hierarchical clustering (Eisen et al., 1998) and correspondence analysis (Fellenberg et al. 2001). Comparison of different visualizations of a dataset are facilitated by shared gene tags. It is also possible to mark all genes bearing a certain keyword like 'cell cycle' in their gene annotation or to import multiple sets of gene tags from text lists.

Statistical analysis of experiment annotations can be applied for arbitrary sets of hybridisations by mouse click, e.g. for those clustered by similar expression profiles. This provides a means to reveal both experimental artefacts and biologically meaningful correlations from huge sets of experimental descriptions in an automated way. The resulting experimental parameters are candidates for being the active players that drive the cells to the expression pattern observed in the hybridisation cluster.

While this is a fairly simple method, it already provides good analytical access to long lists of annotations and huge sets of hybridisations, which could not be thoroughly evaluated by visual inspection. More sophisticated statistical methods can be directly applied, too, because, unlike with free text annotation, instances of occurrence are readily countable for all annotation values.

We consider correspondence analysis particularly useful for the exploratory analysis of microarray data.

Experimental Apparatus

Figure 6A:
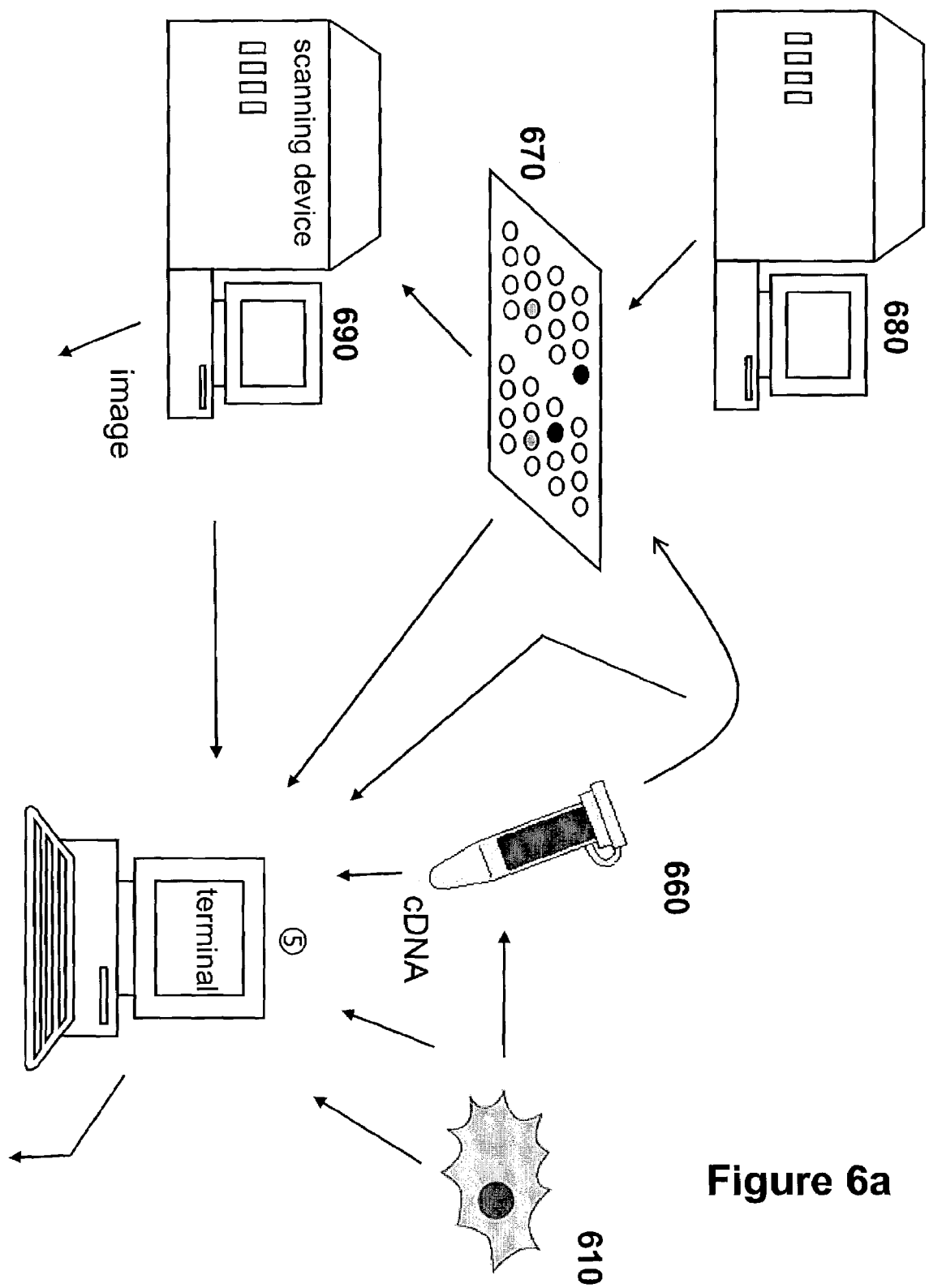
FIG. 6 shows the experimental apparatus used to carry out storage and analysis of the hybridisation data.
Figure 6B:
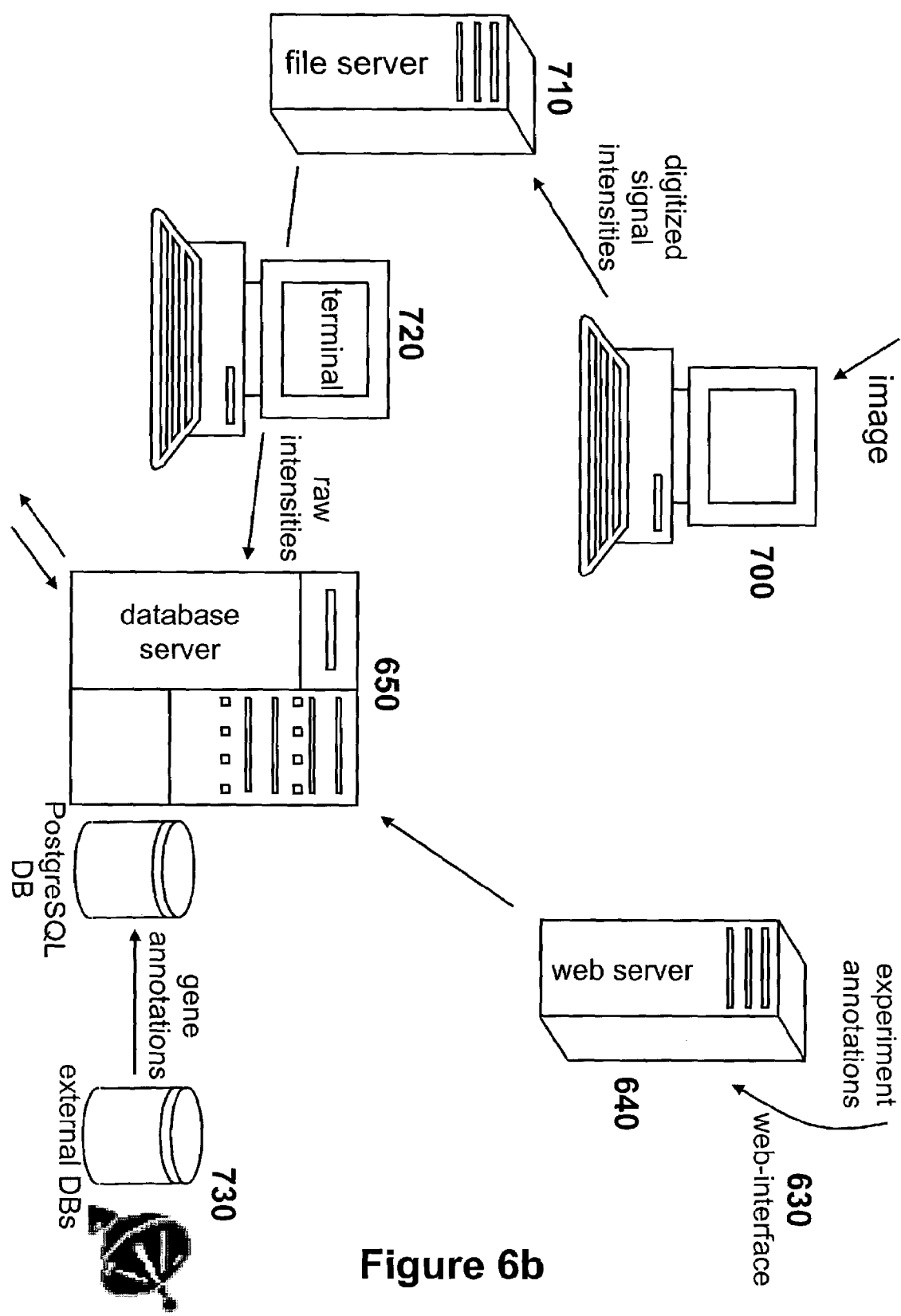
Figure 6C:
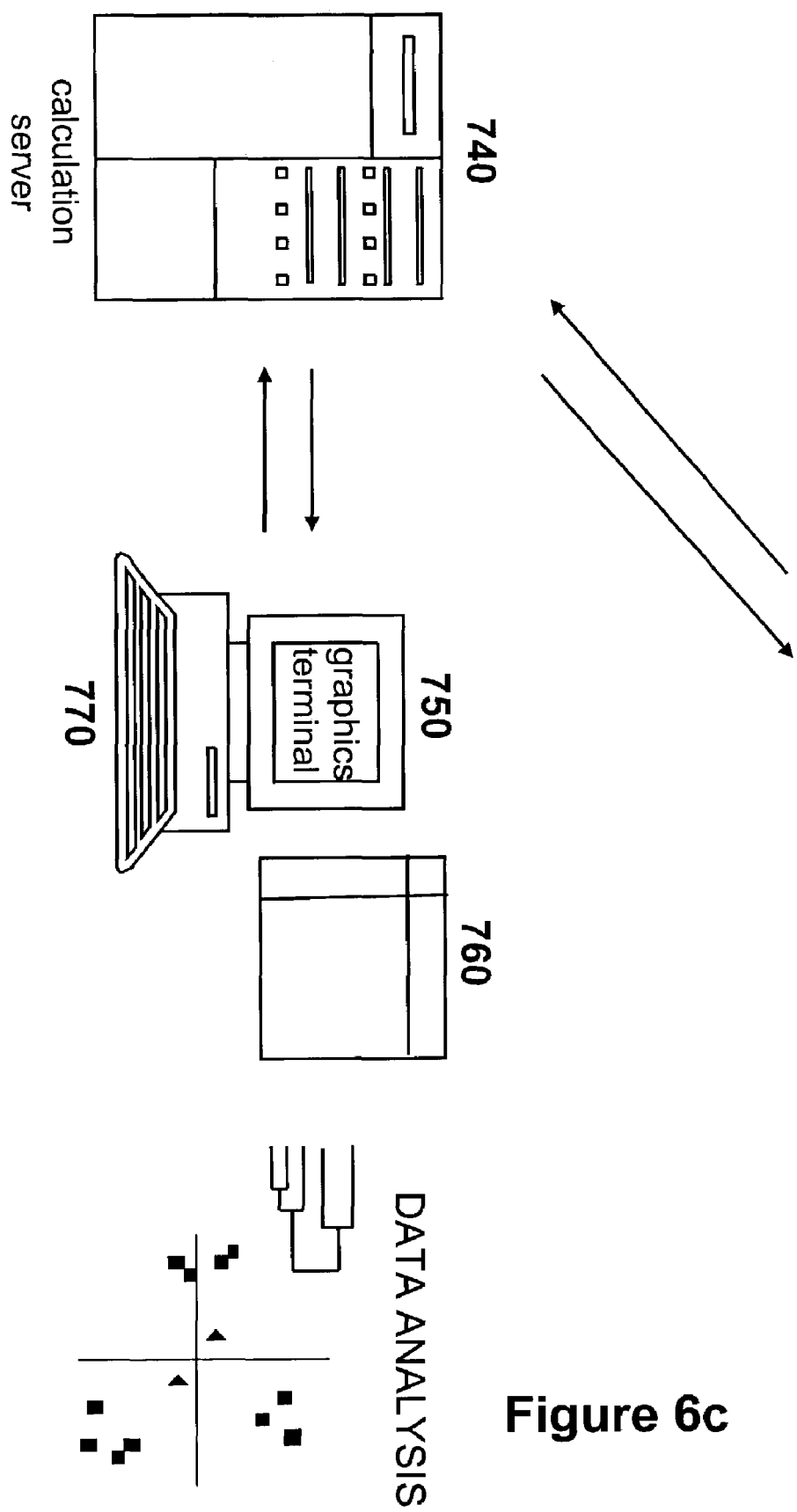

The experimental apparatus required to carry out the experiment is shown in FIG. 6. Cells are grown under specific conditions at 610. The conditions are entered by the experimenter at a terminal 620 through a web interface 630 to web server 640 and stored in a database server 650. The web server 640 is a Sun Ultra 10 workstation running the Apache program. The database server 650 is a Sun E450 server running Postgre SQL.

The mRNA is extracted and reversely transcribed into cDNA and thereby labelled at 660. This is hybridised with spots on the microarray 670. The microarray 670 has been produced by a spotting device 680.

After hybridisation, the microarray 670 is scanned by a scanning device 690 and the image transferred to a computer 700. The computer 700 calculates the digitised signal intensities and stores the digitised signal intensities to a file server 710. The digitised signal intensities, are subsequently uploaded to the database 650.

The database 650 can also obtain external information from external souries 730 such as public databases. Such external information includes, but is not limited to, gene annotations.

A calculation server 740 is provided which analyses the results stored in the database server 650. The results are displayed using a visual display unit 750 running a database browser 760. An input device 770, which might be a keyboard or a mouse, is provided to select values of interest or to input parameters for the statistical analysis.

EXAMPLE

Yeast strain FY1679 (MATa/MATa ura3-52/ura3-52 trp 63/TRP1 leu2 1/LEU2 his3 200/HIS3 GAL2/GAL2) was grown to mid-logarithmic growth phase when the culture was split and hydrogen peroxide added to a final concentration of 200 mM. Samples were taken 5, 10, 15, 20 and 30 min after treatment. Cells were harvested for RNA preparation as described in a paper by Hauser, N. C., Vingron, M., Scheideler, M., Krems, B., Hellmuth, K., Entian, K. & Hoheisel, J. D. (1998) entited "Transcriptional Profiling on all open Reading Frames of *Saccharomyces cerevisae*" published in Yeast 14, 1209-1221. Radioactive labelling by reverse transcription and hybridization to the PCR-based whole genome DNA-array were performed according to the method of the Hauser et al reference.

The raw intensity data as obtained from AIS imaging software (Imaging Research Inc., St. Catherines, Canada) were normalized as described in a paper by Fellenberg, K., Hauser, N. C., Brors, B., Neutzer, A., Hoheisel, J. D., and Vingron, M. (2001) *Proc. Natl. Acad. Sci. U.S.A.* 98, 10781-10786. After normalization the data were filtered for genes fulfilling the following criteria:

Significant absolute intensity, i.e. normalized intensity of at least 5000 in at least one of the hybridizations.

Significant relative change, i.e. normalized intensity divided by the median of normalized intensities for the control hybridizations of at least 4 or $<=1/4$.

Significant reproducibility of this maximum relative change, i.e. minmax separation of at least 1 for at least one of the conditions under study.

508 out of 6103 genes were extracted by these constraints and data table produced. The data have been submitted to correspondence analysis (see FIG. 4), further reducing measurement noise by hybridization-median determined scaling (HMS). Planar embedding explains 76.4% (50.3% without HMS) of the total variance within this dataset, demonstrating the ability of correspondence analysis to show the major variances among the data and overlooking minor changes.

The plot comprises both genes and measurements. The genes are depicted as black dots. Measurements are shown as squares and can be colour-coded according to the experimental condition they belong to. There is one outlying cluster of measurements belonging to the 30-minutes time point, whereas other measurements of the very same condition are located in a distant area, clustering with other time points. Selecting these outliers, searching for at least 2 fold over- or under-represented annotation values results in values belonging to only 8 out of 111 annotations (see FIG. 5).

The first two annotations listed in FIG. 5 provide the information that the entire cluster was hybridised on array individual 6 which is the only one stemming from array series (i.e. production batch) 59, whereas all other arrays were of series 61. From other experiments, we generally observed sufficient comparability among arrays of the same production series, whereas arrays of different batches could not be directly compared.

Alternative Embodiments

The Microarrays of the experiment can be produced using the following spotting devices: SDDC-2 EST, Biogrid, Biocrobitics; Microgrid D; Biorabotics; Omnigrid Genemachines; Qarray Genetix or with solid pins, SMP-3 (Telechem) or Biogrid (Biorobitics) oins.

The scanning devices which can be used include MD Storm 860 phos, MD storm 860 red, MD storm 860 blue, MD 425, MD 475A phos, MD typhoon phos, Fuji BAS 1500, Fuji ELA3000, Biorad Scan Array 3000 GST lumonics, Scan Array 5000 GST lumonics and Axon 4000a.

A number of imaging software pachages can be used including AIS AIDA Image Analyser 3.0, HDG, X Dots Reader, Imagene, Xdigitise, Gene Pix Pro and Quant Array.

The file server 710 can be run under Linux or Windows operating systems.

The terminals 620 can be implemented as Windows, Linux, Sun workstations.

The calculation sever 740 can be a Sun E450, Sun Fire V880 or a mainframe server.

References

Aach, J., Rindone, W., and Church, G. M. (2000). Systematic management and analysis of yeast gene expression data:. Genome Res. 10, 431-445.

Ballard, C., Herreman, D., Schau, D., Bell, R.7 Kim, E., and V31encic, .A. (1998). Data modeling techniques for data warehousing. San Jose, Calif.: IBM International Technical Support Organization, www.redbooks.ibm.com. ISBN 0738402451

Basset Jr., D. E., Eisen, M. B., and Boguski, M. S. (1999). Gene expression informatics—it's all in your mine. Nat. Genet., 21 (Suppl.), 51-55.

Beiβbarth, T., Fellenberg, K., Brors, B., Arribas-Prat, R., Boer, J. M., Hauser, N. C., Scheideler, M., Hoheisel, J. D., Schütz, G., Poustka, A., and Vingron, M. (2000). Processing and quality control of DNA array hybridization data. Bioinformatics, 16, 1014-1022.

Brazma, A., Robinson, A., Cameron, G., and Ashburner, M. (2000). One stop shop for microarray data. Nature, 403, 699-700.

Brown, P. O. and Botstein, D. (1999). Exploring the new world of the genome with DNA microarrays. Nat. Genet., 21(Suppl.), 33-37.

DeRisi, J., Penland, L., Brown, P. O., Bittner, M., Meltzer, P. S., Ray, M., Chen, Y., Su, Y. A., and Trent, J. (1996). Use of a cDNA microarray to analyse gene expression patterns in human cancer. Nat. Genet., 14, 457-460.

Eisen, M. B., Spellnlan, P. T., Brown, P. O., and Botstein, D. (1998). Cluster analysis and display of genome-wide expression patterns. Proc. Natl. Acad. Sci. U.S.A., 95, 14863-14868.

Ermolaeva, O., Rastogi, M., Pruitt, K. D,J Schuler, G. D., Bittner, M. L., Chen, Y., Simon, R., Meltzer, P., Trent, J. M., and Boguski, M. S. (1998).Data management and analysis for gene expression arrays. Nat. Genet., 20, 19-23.

Fellenberg, K., Hauser, N. C., Brors, B., Neutzner, A., Hoheisel, J. D., and Vingron, M. (2001). Correspondence analysis applied to micro array data. Proc. Natl. Acad, Sci. U.S.A., 98, 10781-10786.

Khan, J., Bittner, M., Chen, Y., Meltzer, P. S., and Trent, J. M. (1999). DNA microarray technology: the anticipated impact on the study of human disease. Biochim. Biophys. Acta, 1423) M17-M28.

Lennon, G. G. and Lehrach, H. (1991). Hybridization analyses of arrayed cDNA libraries. Trends Genet., 7,314-317.

Lockhart, D. J., Dong, M., Byrne, M. C., Folletie, M. T., Gallo, M. V., Chee, M. S., Mittmann, M., Wang, C., Kobayashi, M., Horton, H., and Brown, E. L. (1996). Expression monitoring by hybridization to highdensity oligonucleotide arrays. Nat. Biotechnol., 14, 1675-1680.

Lockhart, D. J. and Winzeler, E. A. (2000). Genomics, gene expression and DNA arrays. Nature, 405, 827-836.

Schena, M. (1996). Genome analysjs with gene expression microarrays. BioEssays, 18, 427-431.

Schena, M., Shalon, D., Davis, R. W., and Brown, P. O. (1995). Quantitative monitoring of gene expression patterns with a complementary DNA microarray. Science, 270, 467-470.

Schönbach, C., Kowalski-Saunders, P., and Brusic, V. (2000). Data warehousing in molecular biology. Briefings in Bioinformatics, 1, 190-198.

Shalon, D., Smith, S. J., and Brown, P. O. (1996). A DNA microarray system for analyzing complex DNA samples using two-color fluorescent probe hybridization. Genome Res., 6, 639-645.

Stoeckert, C., Pizarro, A., Manduchi, E., Gibson, M., Brunk, B., Crabtree, J., Schug, J., Shen-Orr, S., and Overton, G. C. (2001). A relational schema for both array-based and sage gene expression experiments. Bioinformatics, 17, 300-308.

What is claimed is:

1. A system comprising:
  a database storage structure for storing data of microarray experiments, said database storage structure being embodied in a computer readable medium, having a plurality of results from experiments on one or more samples, the database structure comprising:
    a definition table comprising rows, wherein each row of the definition table comprises an annotation, a unique identification number and a predefined value, wherein all possible predefined values related to the annotation and its corresponding unique identification number are included in the definition table in separate rows, and wherein said predefined values are identified by an enumerable or countable format and wherein additional annotations are added to the table by addition of one or more rows;
    one or more experiment annotation tables, each table comprising rows, wherein each row comprises an annotation predefined in the definition table stored together with an allowed value as predefined in the definition table; a processing unit for statistically analyzing the results in the database storage structure to produce statistically analyzed results;
  and an output device adapted to produce an output based on said statistically analyzed results.

2. A database storage structure for storing data of microarray experiments, said database storage structure being embodied in a computer readable medium having a plurality of results from experiments on one or more samples, the database structure comprising:
  a definition table comprising rows, wherein each row of the definition table comprises an annotation, a unique identification number and a predefined value, wherein all possible predefined values related to the annotation and its corresponding unique identification number are included in the definition table in separate rows, and wherein said predefined values are identified by an enumerable or countable format and wherein additional annotations are added to the table by addition of one or more rows; and
  one or more experiment annotation tables for storing experimental annotations, each table comprising rows, wherein each row comprises an annotation stored together with an allowed value as predefined in the definition table.

3. The database storage structure of claim 2, wherein the identification numbers are stored as linked lists.

4. The database storage structure of claim 2, wherein the database storage structure comprises one or more result storage tables for storing the results from the experiment in raw form.

5. The database storage structure of claim 2, wherein the database structure comprises one or more gene annotation storage tables for storing annotations of genes.

6. The database storage structure of claim 2, wherein the experiment annotation tables additionally store identifiers to access data in public data bases.

7. The database storage structure of claim 2, wherein the experiment is a microarray experiment and the definition table stores signal intensities of spots of the microarray.

8. The database storage structure of claim 2, comprising one or more subtables for temporarily storing the results from the experiment.

9. A system comprising:
  an experimental apparatus for performing an experiment;
  a storage device for storing the database storage structure of claim 2;
  a processing unit connected to the experimental apparatus for reading the results from the experiment and passing them to the storage device;
  a further processing unit for statistically analyzing the results in the database storage structure to produce statistically analyzed results; and
  a display device for displaying the statistically analyzed results.

10. The system of claim 9, further comprising an input device for entering commands.

11. The system of claim 9, wherein the experimental apparatus comprises a microarray.

12. The system of claim 9, wherein the further processing unit uses statistical analysis methods for analyzing the results in the database storage device.

13. The system of claim 9, wherein the further processing unit uses correspondence analysis methods for analyzing the results in the database storage device.

14. The system of claim 9, wherein the display device includes a web browser.

15. The system of claim 9, further comprising an annotation device.

16. The system of claim 15, wherein the annotation device includes a visual display unit and an annotation input device.

17. The system of claim 9, further comprising a selection device for selecting a subset of the results from the storage device.

18. The system of claim 9, wherein the processing unit initially passes the results to one or more subtables.

19. A method for entering annotations into a database storage structure as claimed in claim 2, comprising:
accessing a definition table to obtain a list of annotations;
using the annotations to generate an input form;
displaying the input form to an annotator;
receiving data input from the annotator;
using the data and a concordance table to generate a set of variables; and
storing the set of variables in the database storage structure.

20. The method of claim 19 further comprising analyzing at least one of the set of variables using correspondence analysis techniques to produce an output set.

21. The method of claim 19 further comprising visualizing the output set.

22. The method of claim 19 wherein the data is derived from a microarray experiment.

23. The method of claim 19, wherein the step of displaying the input form to the annotator is carried out by means of a web browser.

24. The method of claim 19, further comprising selecting at least a subset of the set of variables.

25. The method of claim 19, further comprising clustering the set of variables.

* * * * *